United States Patent
Baldwin et al.

(10) Patent No.: US 10,085,767 B2
(45) Date of Patent: *Oct. 2, 2018

(54) METHODS AND APPARATUSES FOR FLUORO-LESS OR NEAR FLUORO-LESS PERCUTANEOUS SURGERY ACCESS

(71) Applicant: FACULTY PHYSICIANS AND SURGEONS OF LOMA LINDA UNIVERSITY SCHOOL OF MEDICINE, Loma Linda, CA (US)

(72) Inventors: Dalton Duane Baldwin, Loma Linda, CA (US); Alexander Yeo, Colton, CA (US); Jacob Martin, Loma Linda, CA (US)

(73) Assignee: FACULTY PHYSICIANS AND SURGEONS OF LOMA LINDA UNIVERSITY, Loma Linda, CA (US)

(*) Notice: Subject to any disclaimer, the term of this patent is extended or adjusted under 35 U.S.C. 154(b) by 24 days.

This patent is subject to a terminal disclaimer.

(21) Appl. No.: 15/145,631

(22) Filed: May 3, 2016

(65) Prior Publication Data
US 2016/0310165 A1    Oct. 27, 2016

Related U.S. Application Data

(63) Continuation of application No. 14/678,696, filed on Apr. 3, 2015, now Pat. No. 9,351,758, which is a
(Continued)

(51) Int. Cl.
*A61B 17/34* (2006.01)
*A61B 5/06* (2006.01)
(Continued)

(52) U.S. Cl.
CPC ...... *A61B 17/3415* (2013.01); *A61B 1/00147* (2013.01); *A61B 1/00154* (2013.01);
(Continued)

(58) Field of Classification Search
CPC .............. A61B 17/3403; A61B 19/201; A61B 2019/202; A61B 19/5244; A61B 19/5202;
(Continued)

(56) References Cited

U.S. PATENT DOCUMENTS 3,801,205 A    4/1974   Eggenschwyler
4,319,839 A    3/1982   Durran
(Continued)

FOREIGN PATENT DOCUMENTS

WO    WO 2014/197502    12/2014

OTHER PUBLICATIONS

Bilen, et al: "Laser-Assisted Fluoroscopic Puncture: A New Technique for Accessing the Kidney", Journal of Endourology, vol. 17, No. 7, Sep. 2003.
(Continued)

*Primary Examiner* — Amy R Weisberg
(74) *Attorney, Agent, or Firm* — Novel IP

(57) ABSTRACT

A needle access assembly and method for obtaining percutaneous needle access with little or no fluoroscopy. The method can include selecting a target for percutaneous access, directing a laser guide at a desired needle-insertion angle and in line with the selected target, aligning the needle access assembly with the laser, and inserting the needle into the target.

13 Claims, 20 Drawing Sheets

Related U.S. Application Data continuation of application No. 14/295,224, filed on Jun. 3, 2014, now Pat. No. 8,998,943.

(60) Provisional application No. 61/902,090, filed on Nov. 8, 2013, provisional application No. 61/830,585, filed on Jun. 3, 2013.

(51) Int. Cl.

| | | |
|---|---|---|
| *A61B 1/00* | (2006.01) | |
| *A61B 17/00* | (2006.01) | |
| *A61M 25/00* | (2006.01) | |
| *A61B 1/06* | (2006.01) | |
| *A61B 8/08* | (2006.01) | |
| *A61B 6/00* | (2006.01) | |
| *A61M 25/10* | (2013.01) | |
| *A61B 34/20* | (2016.01) | |
| *A61B 90/13* | (2016.01) | |
| *A61B 1/307* | (2006.01) | |
| *A61B 1/018* | (2006.01) | |
| *A61B 6/12* | (2006.01) | |
| *A61B 90/00* | (2016.01) | |

(52) U.S. Cl.
CPC ............ *A61B 1/063* (2013.01); *A61B 1/0676* (2013.01); *A61B 5/061* (2013.01); *A61B 5/065* (2013.01); *A61B 6/485* (2013.01); *A61B 8/0841* (2013.01); *A61B 17/00234* (2013.01); *A61B 17/3403* (2013.01); *A61B 17/3423* (2013.01); *A61B 34/20* (2016.02); *A61B 90/13* (2016.02); *A61M 25/0074* (2013.01); *A61M 25/0097* (2013.01); *A61M 25/10* (2013.01); *A61B 1/018* (2013.01); *A61B 1/307* (2013.01); *A61B 6/12* (2013.01); *A61B 6/487* (2013.01); *A61B 2017/0034* (2013.01); *A61B 2017/00707* (2013.01); *A61B 2017/00853* (2013.01); *A61B 2017/00907* (2013.01); *A61B 2017/3413* (2013.01); *A61B 2034/2055* (2016.02); *A61B 2090/0807* (2016.02); *A61B 2090/3762* (2016.02); *A61B 2090/3966* (2016.02)

(58) Field of Classification Search
CPC ............ A61B 6/485; A61B 2019/5255; A61B 1/00059; A61B 3/0066; A61B 5/150793; A61B 2562/226; A61M 25/0097; A61M 25/10; A61M 2205/60; A61M 2205/6063
USPC .............. 606/1, 108, 129–130, 167–185, 96; 604/264, 116–117, 424, 533–534, 103.06; 600/160, 566–567; 128/898; 359/385–390, 798–800; 116/202, DIG. 5
See application file for complete search history.

(56) References Cited

U.S. PATENT DOCUMENTS

| | | | |
|---|---|---|---|
| 4,651,732 A | 3/1987 | Frederick | |
| 4,674,870 A | 6/1987 | Cain et al. | |
| 5,409,000 A | 4/1995 | Imran | |
| 5,810,841 A | 9/1998 | McNeirney et al. | |
| 6,021,342 A | 2/2000 | Brabrand | |
| 6,041,249 A | 3/2000 | Regn | |
| 6,096,049 A * | 8/2000 | McNeirney | A61B 17/3403 33/286 |
| 6,443,960 B1 | 9/2002 | Brabrand et al. | |
| 6,605,095 B2 | 8/2003 | Grossman | |
| 6,607,477 B1 | 8/2003 | Longton et al. | |
| 6,689,142 B1 * | 2/2004 | Tremaglio, Jr. ... | A61B 17/3403 604/114 |
| 6,810,595 B2 | 11/2004 | Chan | |
| 7,204,826 B2 | 4/2007 | Tremaglio et al. | |
| 7,621,868 B2 * | 11/2009 | Breidenthal ....... | A61B 1/00188 600/166 |
| 8,162,852 B2 | 4/2012 | Norris | |
| 8,454,586 B2 | 6/2013 | Anastasie | |
| 8,715,233 B2 * | 5/2014 | Brewer ............ | A61M 25/0612 600/424 |
| 8,998,943 B2 | 4/2015 | Baldwin et al. | |
| 9,351,758 B2 | 5/2016 | Baldwin et al. | |
| 2003/0120154 A1 | 6/2003 | Sauer et al. | |
| 2004/0106934 A1 | 6/2004 | Grossman | |
| 2005/0256451 A1 | 11/2005 | Adams et al. | |
| 2007/0100234 A1 | 5/2007 | Arenson et al. | |
| 2007/0100299 A1 | 5/2007 | Magnusson | |
| 2008/0146915 A1 | 6/2008 | McMorrow | |
| 2008/0146939 A1 | 6/2008 | McMorrow et al. | |
| 2011/0172520 A1 | 7/2011 | Lentz | |
| 2012/0022504 A1 | 1/2012 | Epshtein et al. | |
| 2012/0022508 A1 | 1/2012 | Gross et al. | |
| 2012/0123204 A1 | 5/2012 | Wynberg | |
| 2012/0316500 A1 | 12/2012 | Bierman et al. | |
| 2013/0018254 A1 | 1/2013 | Drucker | |
| 2014/0107473 A1 | 4/2014 | Dumoulin et al. | |
| 2014/0357986 A1 | 12/2014 | Baldwin | |
| 2014/0357987 A1 | 12/2014 | Baldwin | |
| 2015/0272701 A1 | 10/2015 | Baldwin | |

OTHER PUBLICATIONS

Blair, et al.: "Reduced Fluoroscopy Protocol for Percutaneous Nephrostolithotomy: Feasibility, Outcomes and Effects on Fluoroscopy Time", The Journal of Urology, vol. 190, Dec. 2013, pp. 2112-2116.
Brisbane, et al.: "Fluoro-less Ureteral Stent Placement Following Uncomplicated Ureteroscopic Stone Removal: A Feasibility Study", Urology 80 (4), Oct. 2012, pp. 766-770.
Greene, et al.: "Comparison of a Reduced Radiation Fluoroscopy Protocol to Conventional Fluoroscopy during Uncomplicated Ureteroscopy", Urology 79 (2), Aug. 2011, pp. 287-290.
Hawkins et al.: "Combined Retrograde/Antegrade Nephrostomy Technique," Journal of Endourology, vol. 1, No. 4, 1987.
Hsi et al.: Fluoroless Ureteroscopy: Zero-Dose Fluoroscopy During Ureteroscopic Treatment of Urinary-Tract Calculi, Journal of Endourology, vol. 27, No. 4, Apr. 2013, pp. 432-437.
Ko, et al.: "C-Arm Laser Positioning Device to Facilitate Percutaneous Renal Access", Surgeon's Workshop, Urology 70 (2), Aug. 2007.
Kokorowski, et al.: Prospective Systematic Intervention to Reduce Patient Exposure to Radiation During Pediatric Ureteroscopy, The Journal of Urology, vol. 190, 1747-1478, Oct. 2013.
Kroes, et al.: Assessment of Needle Guidance Devices for Their Potential to Reduce Fluoroscopy Time and Operator Hand Dose during C-Arm Cone-Beam Computed Tomography-guided Needle Interventions, J Vasc Intery Radiol, Jun. 2013; 24:901-906.
Krupp, et al.: "Fluoroscopic Organ and Tissue-Specific Radiation Exposure by Sex and Body Mass Index During Ureteroscopy", Journal of Endourology, vol. 24, No. 7, Jul. 2010, pp. 1067-1073.
Nguyen, et al.: "In Automated Fluoroscopy Settings, Does Shielding Affect Radiation Exposure to Surrounding Unshielded Tissues?", Journal of Endourology, vol. 26, No. 11, Nov. 2012.
Shuler et al.: "Laser Targeting With C-Arm Fluoroscopy: Effect on Image Acquisition and Radiation Exposure," J Orthop Trauma, vol. 27, No. 5, May 2013. pp. e97-e102.
Smith, et al.: "Radiation Exposure During Continuous and Pulsed Fluoroscopy", Journal of Endourology, vol. 27, No. 3, Mar. 2013, pp. 384-388.

* cited by examiner

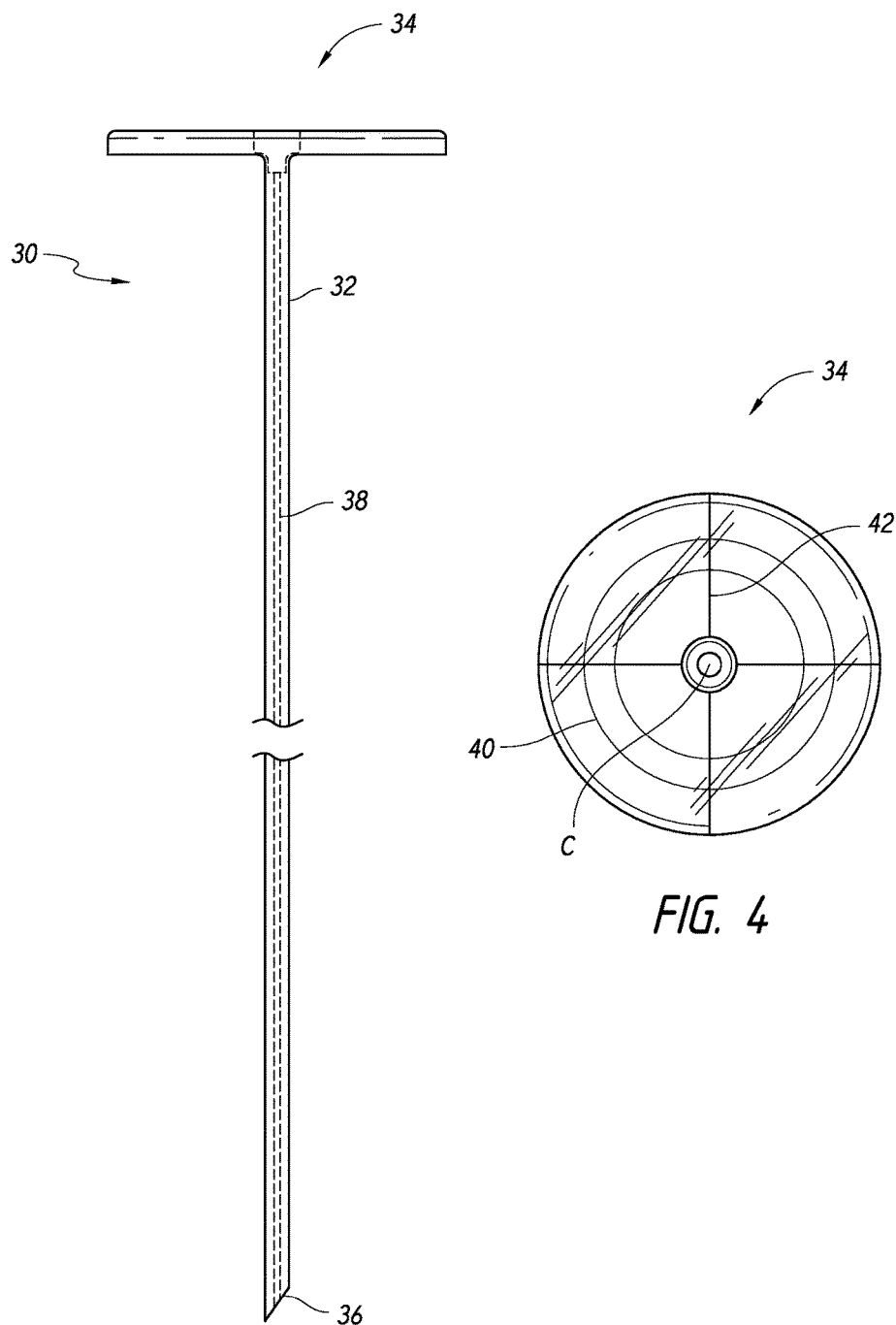

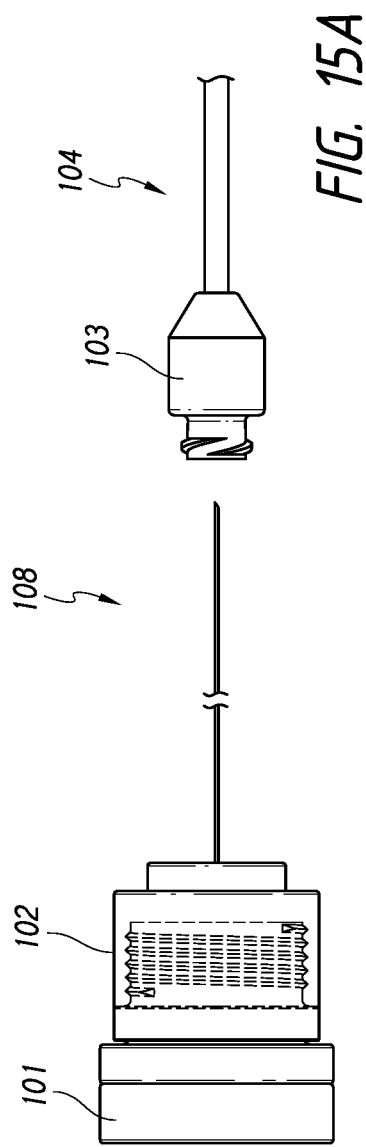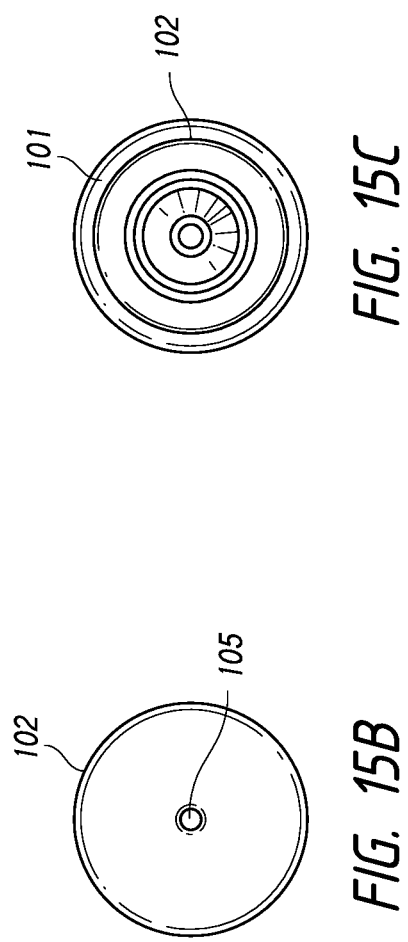
FIG. 15A
FIG. 15B
FIG. 15C

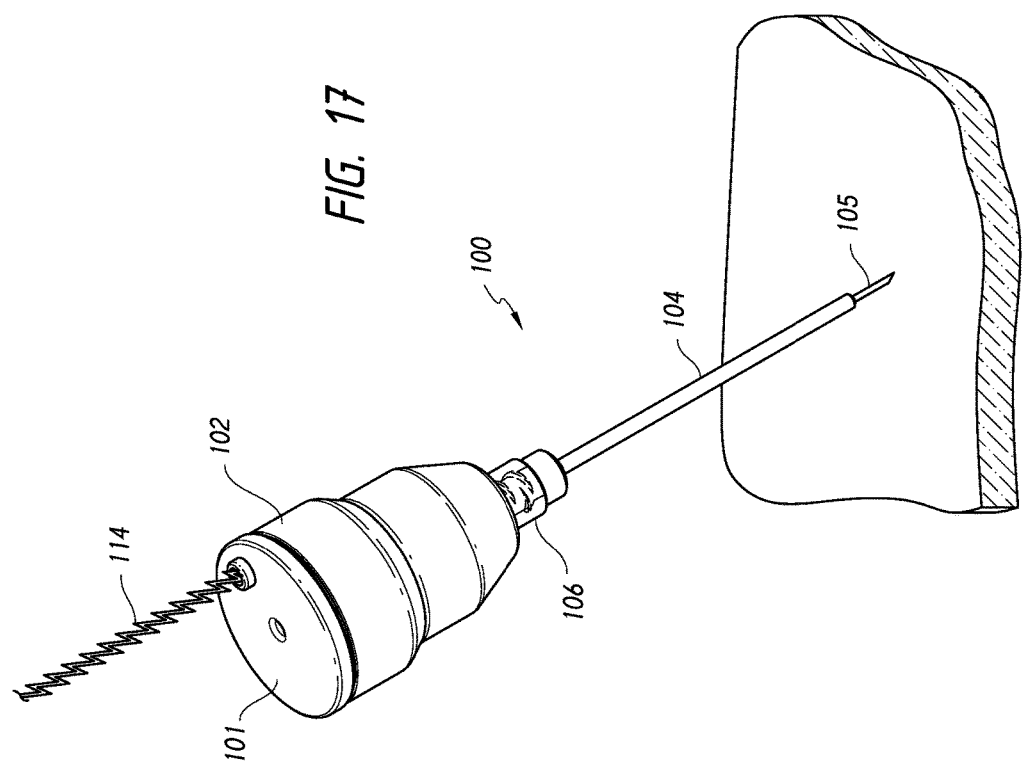

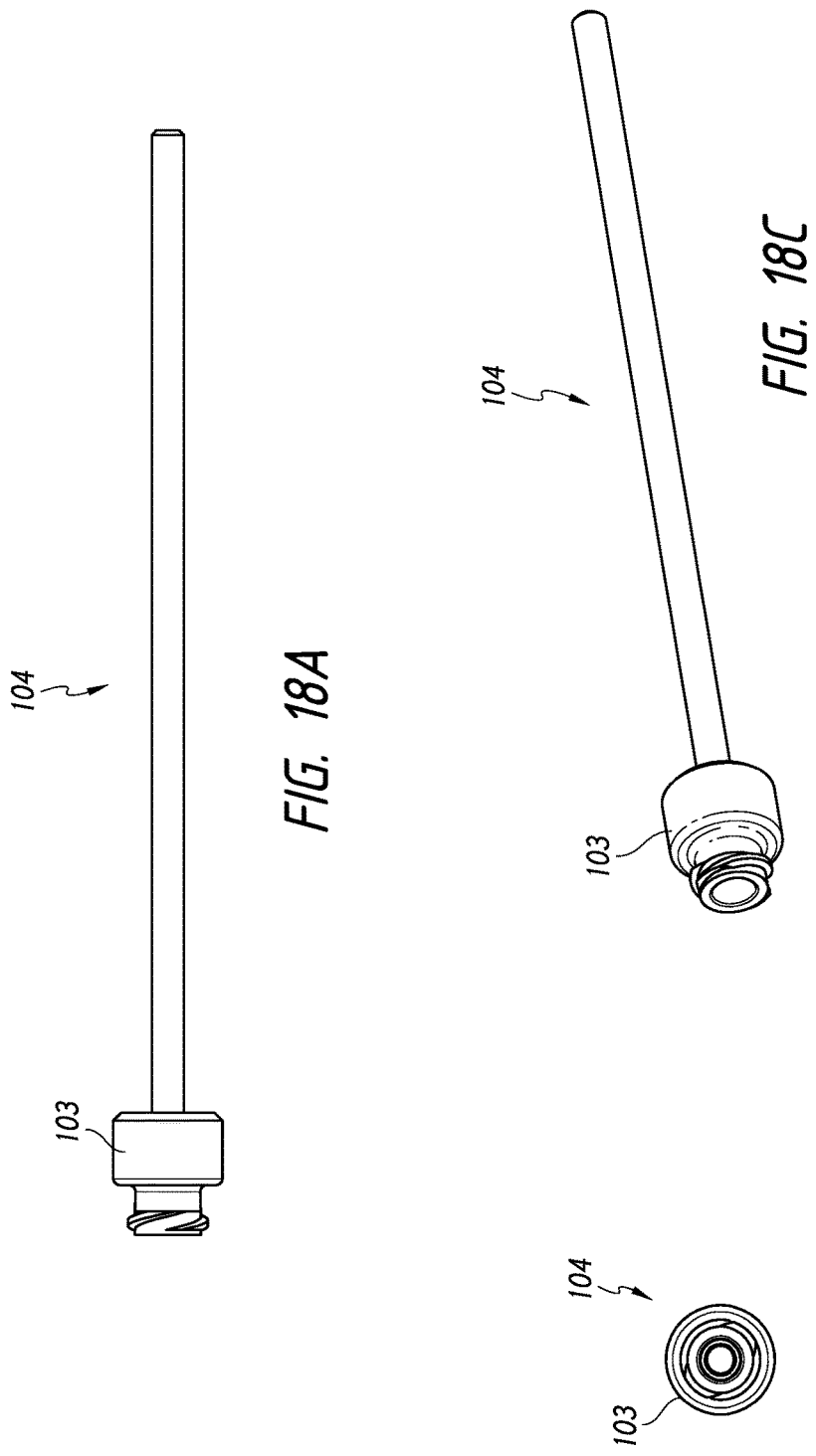

METHODS AND APPARATUSES FOR FLUORO-LESS OR NEAR FLUORO-LESS PERCUTANEOUS SURGERY ACCESS

INCORPORATION BY REFERENCE TO ANY PRIORITY APPLICATIONS

This present application is a continuation of U.S. application Ser. No. 14/678,696, filed Apr. 3, 2015, titled METHODS AND APPARATUSES FOR FLUORO-LESS OR NEAR FLUORO-LESS PERCUTANEOUS SURGERY ACCESS, now U.S. Pat. No. 9,351,758, which is a continuation of U.S. application Ser. No. 14/295,224, filed Jun. 3, 2014, titled METHODS AND APPARATUSES FOR FLUORO-LESS OR NEAR FLUORO-LESS PERCUTANEOUS SURGERY ACCESS, now U.S. Pat. No. 8,998,943, which claims priority benefit under 35 U.S.C. § 119(e) to U.S. Provisional Application No. 61/830,585, filed Jun. 3, 2013, titled METHOD FOR FLUORO-LESS OR NEAR FLUORO-LESS PERCUTANEOUS SURGERY ACCESS, and U.S. Provisional Application No. 61/902,090, filed Nov. 8, 2013, titled METHOD FOR FLUORO-LESS OR NEAR FLUORO-LESS PERCUTANEOUS SURGERY ACCESS, both of which are hereby incorporated by reference in their entirety.

Any and all applications for which domestic priority claim is identified in the Application Data Sheet as filed with the present application are hereby incorporated by reference under 37 CFR 1.57.

BACKGROUND

Field

The present disclosure relates to percutaneous surgery access.

Description of the Related Art

Percutaneous access is a commonly used step for the treatment and or testing of a variety of diseases and conditions in a plethora of surgical and clinical procedures. An initial step in many forms of percutaneous surgery is the insertion of a wire for later access into the inner portion of a lumen, space, viscous, or organ. An example of this type of access could be placement of a needle through the skin into the kidney for access into one of the calices of the kidney. This step of the percutaneous procedure is often one of the most difficult steps and often requires real-time, imaging guidance with ultrasound, CT, or fluoroscopy.

SUMMARY

Conventional techniques for needle placement require the use of continuous fluoroscopy during the insertion of the needle into the collecting system. Due to the depth of the tissues surrounding the kidney and the variation of the renal position caused by ventilation the surgeon is asked to hit a small moving target positioned deep inside the body and slight imprecision in needle positioning may lead to complete failure to access the desired space. Subsequently, surgeons are required to grasp a needle using either their hands (placing their hands directly inside the fluoroscopy beam), or using a needle holder or device for holding the needle (decreasing their control and ability to perceive tactile subtle cues regarding tissue densities).

Fluoroscopy guidance accounts for a substantial percentage of the procedural radiation exposure to the patient as well as the surgical team. Every patient poses a different challenge and significant amounts of fluoroscopy can be used to navigate the trocar needle through the patient's anatomy. During needle placement, the amount of fluoroscopy required to obtain access is often several minutes and may be greater than 60 minutes of fluoroscopy time. 60 minutes (60 mSy) of fluoroscopy may be associated with significant radiation exposure and depending upon the location of the fluoroscopy beam and the size of the patient may exceed the recommended yearly occupational exposures of radiation. The deterministic effects of radiation occur quickly following exposure and may include sterility, cataracts, skin erythema, and/or damage to the blood production system, intestinal function, or neurologic function. In contrast, the stochastic effects of radiation are not directly dose dependent and may occur at any time following radiation exposure and may include genetic damage, cancer, and mental effects. High levels of radiation exposure have been recognized as a potential carcinogenic risk to the patient since the high-energy radiation may cause DNA mutation. It has been shown that a few minutes of fluoroscopy time at standard settings will confer a $\frac{1}{1,000}$ risk of developing fatal cancer. For every 1000 patients exposed to even 10 mSv of radiation, one of those will develop cancer as a result. See Sodickson, A., Baeyens, P. F., Andriole, K. P. et al., Recurrent CT, cumulative radiation exposure, and associated radiation-induced cancer risks from CT of adults. Radiology, 251: 175, 2009. Further, fluoroscopy exposure is also known to have a cumulative effect over time, increasing the risk of stochastic effects on both the patient and the staff members, including the physician. As there is no safe lower limit (no safe threshold), below which no risk for cancer will occur and since the higher the exposure the greater the risk, it is important to decrease the radiation exposure of patients during percutaneous access.

Certain aspects of the present disclosure are directed toward a device that, when paired with a guidance system, may it be a laser or any image guided methods of needle placement such as ultrasound, ionizing radiation (fluoroscopy, plain film x-ray), computerized tomography, or magnetic resonance imaging, can deliver accurate and precise placement of a needle. When the device is aligned between the imaging system and the target, the device provides visual confirmation of alignment to the user and "paints" the target to facilitate precise insertion of a trocar-cannula needle.

Certain aspects of the present disclosure are directed toward a method of obtaining percutaneous needle access. The method can include selecting a calix for percutaneous access; positioning a flexible ureteroscope in the selected calix; directing a laser guide at a desired needle-insertion angle and in line with a tip of the ureteroscope; aligning a needle with the laser and the ureteroscope tip; and inserting the needle into the selected calix. In certain aspects, if necessary, fluoroscopy can be applied for less than about ten seconds. In other aspects, this method and devices may allow incremental reduction in radiation exposure of 5-10%. In other aspects, this reduction might be between 5 and 99%.

The above-mentioned method can include delivering an instrument to the selected calix. The instrument can be configured to facilitate the insertion of the needle into the selected calix. In certain aspects, the instrument can be identifiable under ultrasound. In certain aspects, the instrument can be a balloon catheter. In certain aspects, the instrument can be a basket catheter.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIG. 3 illustrates an exemplary embodiment of a needle.

FIG. 4 illustrates a top view of the needle shown in FIG. 3 having concentric rings to provide a target for laser guidance.

FIG. 15A illustrates a side view of another embodiment of a needle access assembly having a trocar needle and a cannula.

FIG. 15B illustrates a distal end view of the trocar needle shown in FIG. 15A.

FIG. 15C illustrates a proximal end view of the trocar needle shown in FIG. 15A.

FIG. 17 illustrates a perspective view of the assembly shown in FIG. 16 indicating that the assembly is not properly aligned.

FIG. 18A illustrates a side view of an exemplary embodiment of a cannula.

FIG. 18B illustrates an end view of the cannula shown in FIG. 18A.

FIG. 18C illustrates a perspective view of the cannula shown in FIG. 18A.

DETAILED DESCRIPTION

Figure 1:
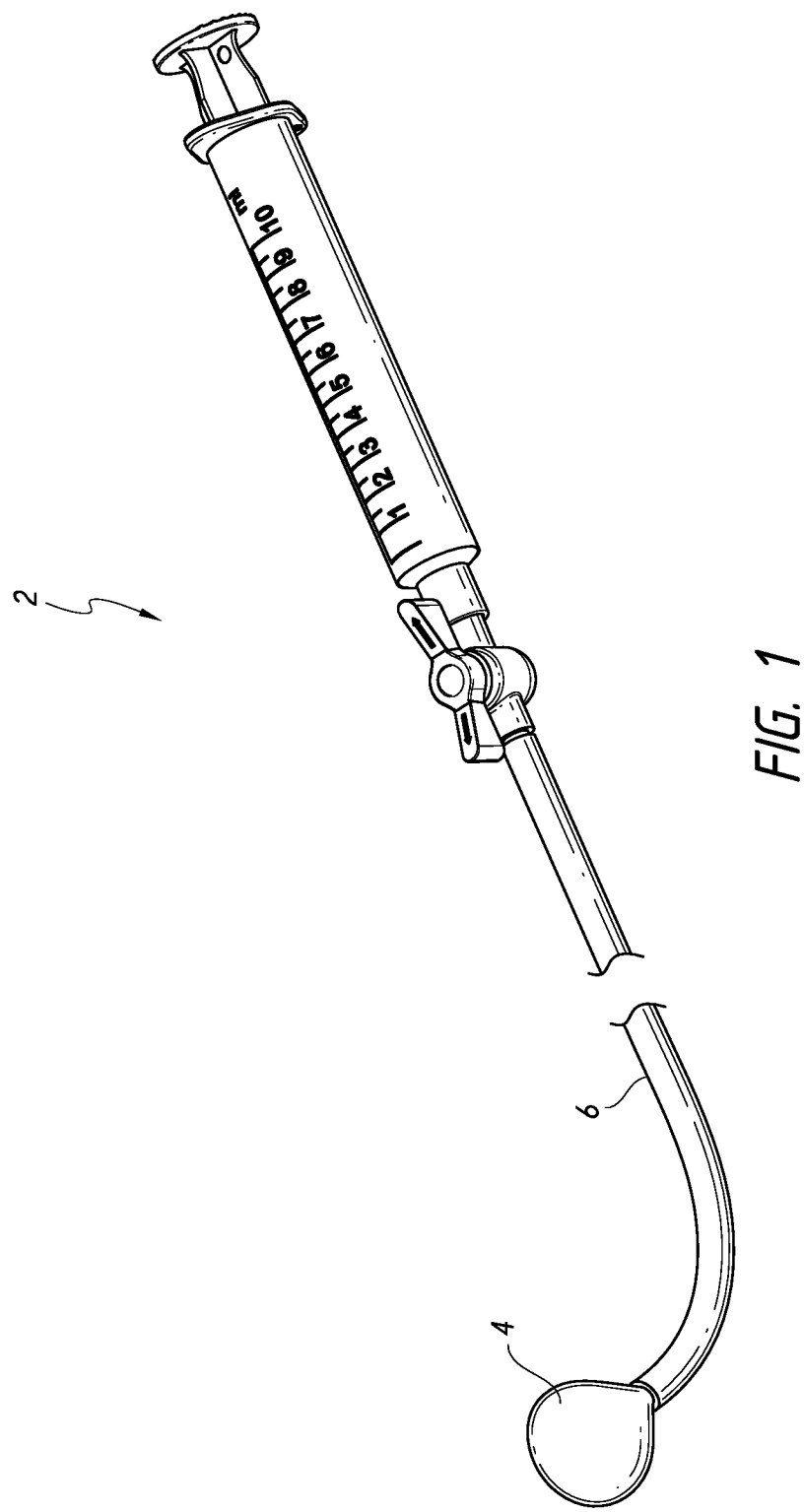
FIG. 1 illustrates an exemplary balloon catheter that can be used with the methods described herein.

The following discussion is presented to enable a person skilled in the art to make and use one or more embodiments of the invention. The general principles described herein may be applied to embodiments and applications other than those detailed below without departing from the spirit and scope of the invention. Therefore the present disclosure is not intended to be limited to the embodiments shown, but is to be accorded the widest scope consistent with the principles and features disclosed or suggested herein.

Given the risks associated with fluoroscopy exposure described above, there is a need to reduce procedural ionizing radiation. One such solution is to reduce fluoroscopy use during percutaneous access to tissue, while simultaneously maintaining accurate needle placement. As such, there is a need for a device that will allow precision and accuracy without continuous fluoroscopy use for recurrent visualization.

The devices and methods described herein are designed to simplify procedures for percutaneous access and significantly reduce radiation exposure to the surgeon, patient, and staff members. Although the disclosure below is discussed in connection with the kidneys, the methods and devices described herein can be used to obtain access to other structures, lumens, organs, and spaces.

Method of Inserting an Ureteroscope without Image Guidance

Placing a needle into the kidney for renal access for stone surgery will be used as an example of this technique. However, similar concepts and principles would also apply to other procedures, such as placing probes into the kidney to treat a renal cancer, placing access into an infected fluid collection for drainage of an abscess, placing tubes into any space to serve as a drain, (i.e., pleural space, peritoneal drain, cholecystectomy drain, bladder drain, lymphocele drain, pericardial space, etc.).

In describing the percutaneous access into the kidney as an example, the patient can be positioned into a prone and split-legged position to allow simultaneous access into the kidney and the urethra. Using a flexible cystoscope, the surgeon can place a guide wire into the kidney to allow later insertion of an ureteroscope into the kidney. After positioning the first guide wire, the surgeon can optionally position a dual lumen type catheter in the kidney to allow the placement of a second guide wire, so there can be both a working wire and a safety wire positioned in the kidney. In certain aspects, the guide wires can be placed into the kidney in a retrograde fashion using no image guidance at all. The two guide wire lengths can be compared to confirm that both wires were correctly positioned in the kidney.

The working and/or safety guide wires can include one or more of the following features. In certain aspects, the guide wire can be an angle-tipped guide wire that has a lubricious coating to allow it to slip easily above any ureteral obstruction. In certain aspects, the guide wire can include one or more features to facilitate visualization. For example, the guide wire can be designed to produce a highly echogenic profile allowing it to be easily visualized using ultrasound. In one configuration, the shaft may be rounded at the tip to allow easier insertion but have a flattened shape proximal to the tip (e.g., about 1 to 5 cm proximal to the tip of the wire) to allow the wire to be more easily seen under ultrasound guidance. The flattened surfaces of the wire may reflect the acoustic beams back at a similar angle to allow the wire to be easily seen under ultrasound. This wire may also be easily seen under very low dose fluoroscopy levels. As another example, the guide wire can include one or more radiopaque markers to enhance fluoroscopic visualization. The guide wire may have interval marks (e.g., placed every one cm) to allow insertion of these wires under endoscopic visualization. For example, the wire might be black with white markings identifying the distances. As another example, the wire could be white with blue markings identifying the length marks. The colors could be any color that would allow easy identification endoscopically and externally. In certain aspects, the guide wire can include a nitinol core and/or a PTFE coating. In certain aspects, the guide wire may include a lubricious coating to allow easy insertion. In certain aspects, the wire could include a retractable square outer sheath through which the guide wire could be placed into the kidney to allow appropriate placement and then the acoustically dense sheath passed over the wire to allow even the tip to be seen easily under ultrasound. In certain aspects, the guide wire could be etched with an acoustically dense surface to allow the wire to be seen easily under ultrasound guidance. In one configuration, the guide wire might be an Amplatz extra stiff type wire that is floppy at both ends to allow the insertion of the flexible ureteroscope without trauma to the ureteroscope or the kidney. In certain aspects, the guide wire can be a standard 0.035 or 0.038 Teflon-coated guide wire or a lubriciously coated guide wire.

The surgeon can advance a flexible ureteroscope over the working wire into the ureter using a fluoro-less technique. The technique for insertion of the ureteroscope is particularly important to prevent the migration of ureteral stones outside of the ureter, and to facilitate correct positioning of the ureteroscope. In general, if recent imaging shows no ureteral stones the ureteroscope will be placed over the working wire and advanced until the ureteroscope tip is in the proximal ureter a distance of 15 to 20 cm in a female and 30-35 cm in a male with normal sized phallus. If recent imaging shows a mid-ureteral stone, the flexible ureteroscope will only be advanced into the distal ureter. If recent imaging shows only a distal ureteral stone, the flexible ureteroscope will be advanced just through the ureteral orifice.

The actual passage of the ureteroscope may occur in several ways. In one method, the surgeon advances the ureteroscope tip over the wire while the assistant holds the handle of the ureteroscope and the wire in a steady and fixed position. This allows the surgeon to delicately feel the tactile feedback from the points of resistance as the ureteroscope is advanced over the wire including the urethral sphincter, bladder neck, and ureteral orifice. If resistance is met at the appropriate depth for the ureteral orifice (and the ureteroscope does not progress), the ureteroscope is pulled back 2-3 cm and rotated 90 degrees and another attempt at advancement is made. If this is not successful, the ureteroscope can be pulled back another 2-3 cm and rotated in the same direction another 90 degrees before another attempt is made. This is repeated until the ureteroscope has returned back to the original starting position. If the ureteroscope has rotated 360 degrees and there has been no passage through the ureteral orifice a Foley will be inserted into the bladder in order to empty the bladder and the process repeated in its entirety.

In another method, the ureteroscope may be passed with the light cord and camera connected so that some subtle visual details may be obtained as the ureteroscope is advanced up the ureter.

In a third method the ureteroscope might be advanced using a "bare naked" technique up the ureter without the use of a safety wire and the ureteroscope used as the safety channel itself. In this technique normal saline or any other irrigation fluids would be injected under pressure to provide visualization of the important anatomic structures. If the ureteroscope has difficulty engaging the ureteral orifice a guide wire could be inserted into the ureteral orifice to help engage the ureteroscope tip into the ureter and the ureteroscope could then be advanced into the ureter under direct vision.

With all the techniques, once the ureteroscope was positioned in the ureter it would slowly be advanced up the ureter in a retrograde fashion from the point of insertion under direct vision. This flexible ureteroscope would then be advanced slowly in a retrograde fashion from the point of insertion either until a stone was encountered or until the renal calices were identified.

The next step in the ureteroscopic-assisted form of the Laser DARRT technique is for the surgeon under direct endoscopic vision to select the desired calix for percutaneous access of the collecting system. After selecting the ideal calix for puncture, the surgeon can determine the optimal access tract using CT, ultrasound, or fluoroscopic guidance.

Fluoroscopy can optionally be performed with a single pulse or a pulse rate of one pulse per second to visualize the tip of the ureteroscope. The ureteroscope is very dense and can be seen easily at even very low mA and kVp settings. One pulse per second is significantly lower than the conventional pulse rate, which can be about 25 to about 30 pulses per second.

In certain aspects, after the calix that provides the best access to the kidney has been selected ureteroscopically, ultrasound can be used to map out the pleura, lung, and intra-abdominal organs. Assuming that there are no organs in the way and that the lung is a safe distance away from the puncture site, the needle can be inserted directly under ultrasound guidance into the desired calyx. In some configurations, the needle can be between 14 and 25 gauge, e.g., between about 18 gauge and 20 gauge. In another approach, the needle can be passed into the desired calyx using a "free hand" approach or the needle could be directed using a guide that directs the needle into the desired calyx and is attached to an US probe, CT scanner, or MRI scanner. For example, a special instrument can be used to provide an acoustically dense image to simplify targeting under US guidance. As shown in FIG. 1, this acoustically dense structure could be a balloon catheter 2 configured for identification under ultrasound. The balloon 4 can be inflated with air or ultrasonic contrast material or alternatively with saline to provide a fluid filled target.

The balloon catheter 2 can be configured for insertion through a flexible ureteroscope channel. The balloon catheter shaft 6 can be between about 0.5 F and about 3.3 F. In certain aspects, the shaft can be about 2.2 F. The balloon can be made of a strong and expandable polymer, such as silicone, latex, vinyl, Gore-tex®, or any other expandable coverings. The balloon material could be acoustically similar to saline or could be acoustically dense to provide a dense target. Once the needle has been inserted into the calyx, the balloon can be deflated and removed through the ureteroscope. In some embodiments, a ureteral access sheath can be placed and then the balloon can be removed with the ureteroscope through the ureteral access sheath.

Figure 2:
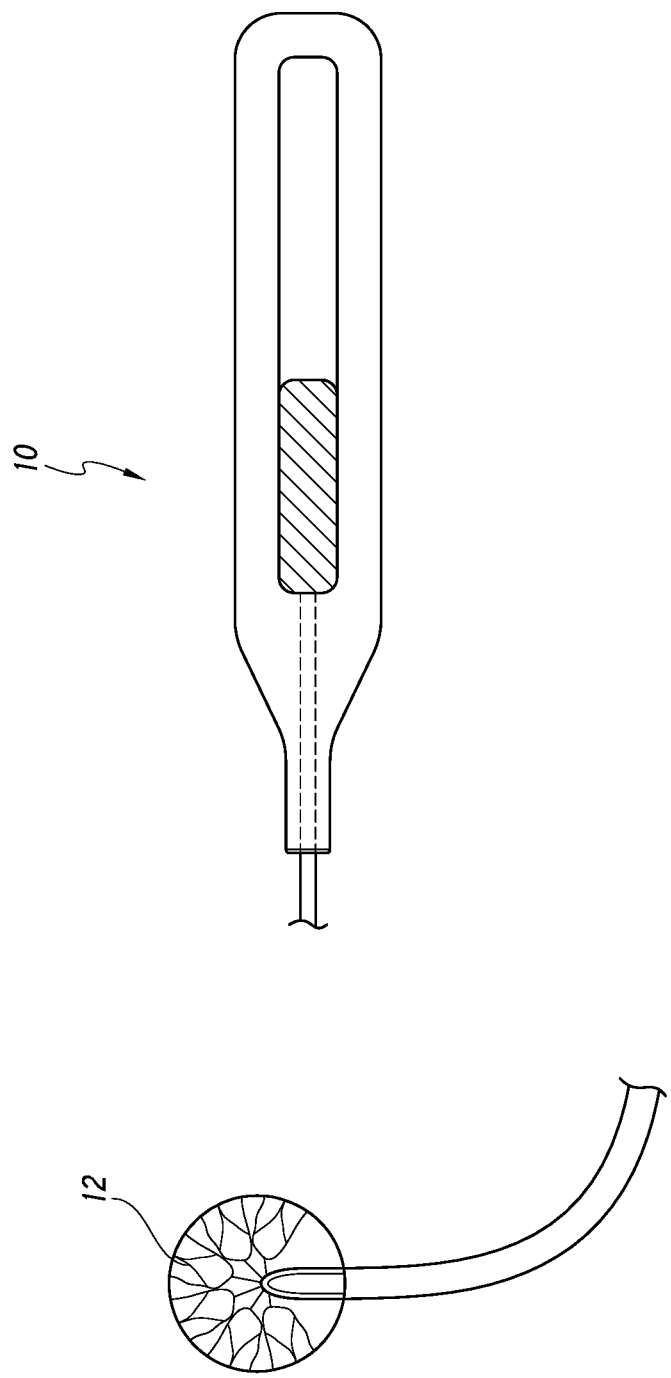
FIG. 2 illustrates an exemplary basket catheter that can be used with the methods described herein.

In certain aspects, the acoustically dense instrument can be a basket catheter. FIG. 2 illustrates an exemplary basket catheter 10 designed to create an acoustic interface. The basket 12 can be formed from an acoustically dense material or metal, such as Nitinol. In an expanded configuration, the basket 12 can form, for example, a large open sphere having an expanded diameter between about 1 mm and about 20 mm. In certain aspects, the expanded diameter can be about 10 mm. In some configurations of this device, a small gauge wire can be inserted percutaneously, directly into the basket 12 under ultrasound guidance and then the basket 12 can close over the wire to allow the wire to be pulled into the proximal ureter. Once the small wire is in the proximal ureter, past the stone, a sheath can be inserted over the wire to allow conversion to a larger 0.035 or 0.038 guide wire for subsequent dilation.

In some methods, the respirations can be paused by the anesthesiologist after a period of hyperventilation. For example, the respirations can be routinely paused during end expiration to move the lungs as far away as possible from the site of needle access. As another example, the respirations can be held during other parts of the respiratory cycle, for example, during inspiration to move the kidney below the rib.

In another embodiment of this technique, fluoroscopy can be used to help direct the needle into the desired calyx instead of using Ultrasound. An external instrument can be used to provide an obvious target to assist in targeting the correct calix and positioned on the skin in the path of the fluoroscopy beam such that the beam would align with the tool on the skin and the calyx desired for puncture.

Using a C-arm placed at about 0 to about 45 degrees of oblique rotation, or between about 15 degrees and about 30 degrees of oblique rotation, such as about 30 degrees, the surgeon can use a heavy clamp to determine the skin site that will lead to the desired trajectory for PCNL insertion. For example, after using the C-arm to generate an x-ray image and identifying the target location based on the image, the surgeon can mark the target using a clamp or other dense, metal instrument. Use of the instrument to mark the target access position is optional.

Figure 8A:
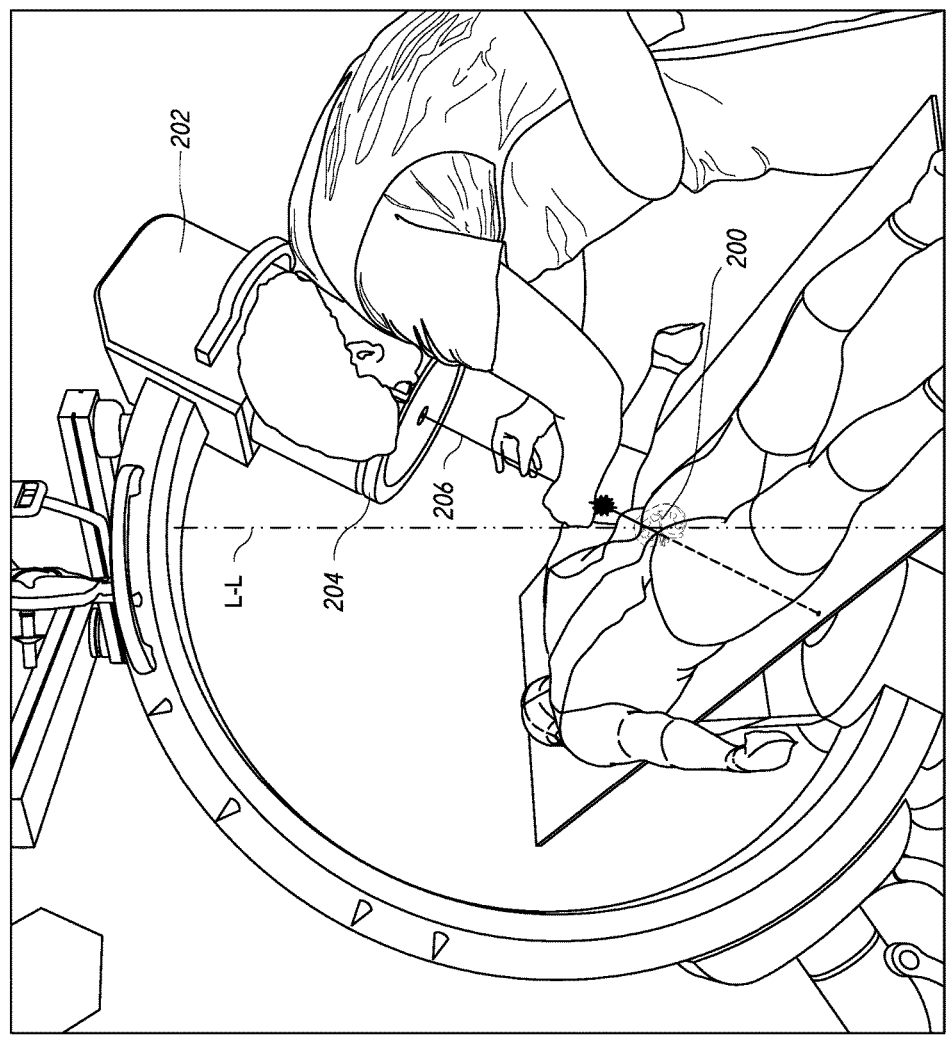
FIGS. 8A-8D illustrate a method for laser-guided percutaneous access.

As shown in FIG. 8A, the C-arm 202 can include a laser guide 204 attached to the head of the C-arm beam. The laser guide can be configured to facilitate the alignment and insertion of the needle 208 (see FIGS. 8B-8D) without fluoroscopy or with decreased fluoroscopy and without other image guidance. The surgeon can direct the laser guide 204 at the desired needle-insertion angle, for example, in line with the tip of the clamp or other marker on the skin and the ureteroscope inside the desired calix selected for puncture. The desired needle-insertion angle can be at least about 0 degrees and/or less than or equal to about 45 degrees relative to the vertical axis L-L, for example, between about 0 degrees and 30 degrees or between 15 degrees and 45 degrees, such as about 30 degrees.

Figure 8B:
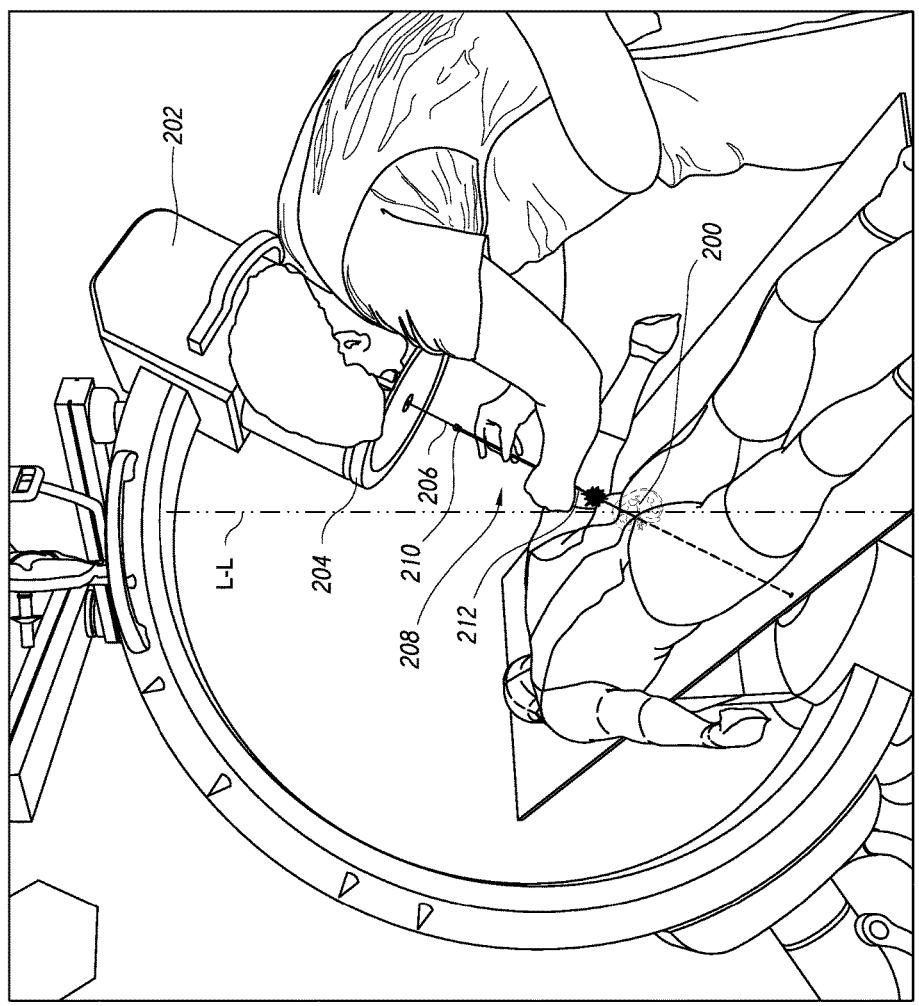
Figure 8C:
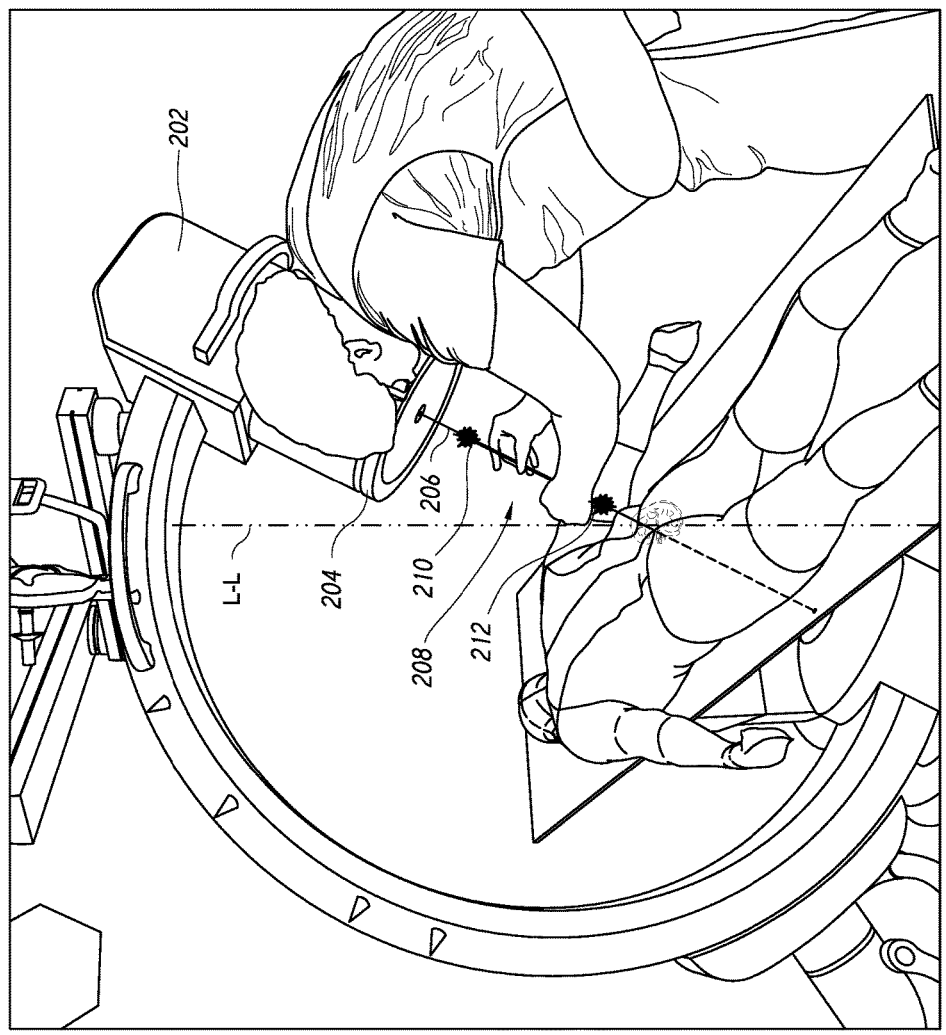
Figure 8D:
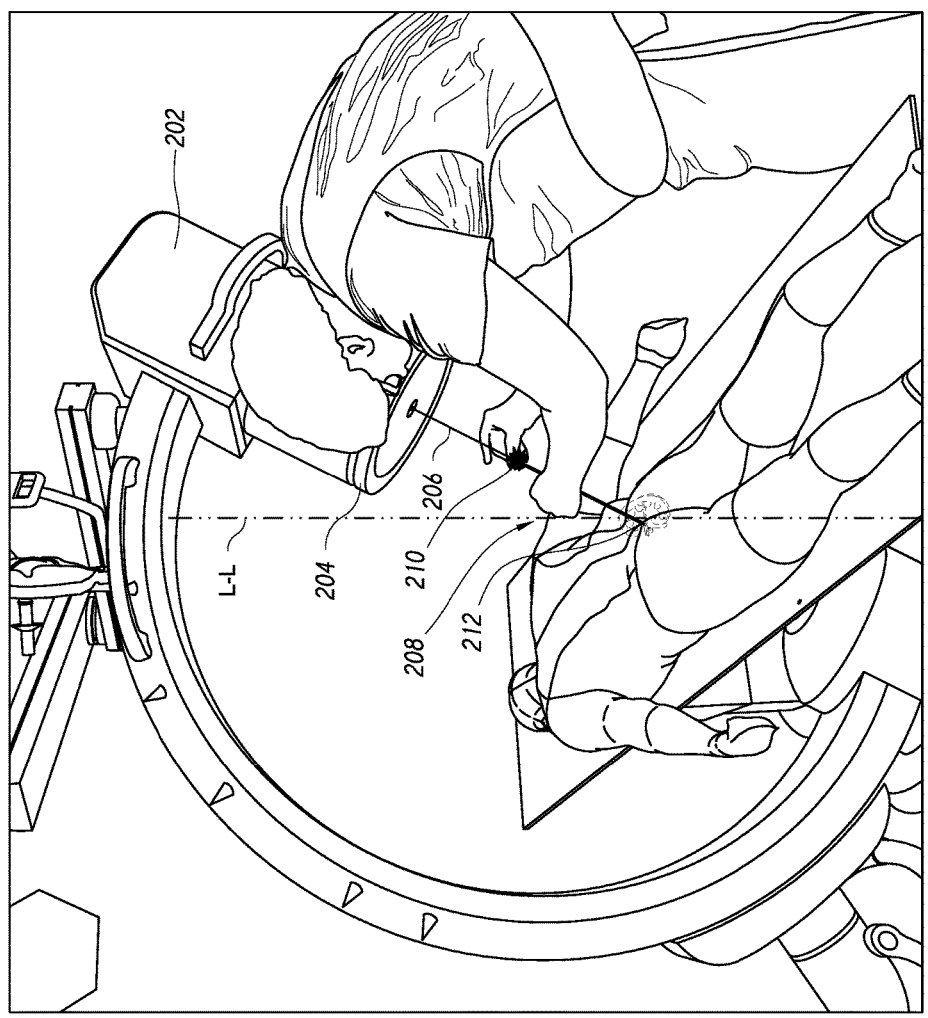

After the laser beam 206 is directed at the desired access location and angle, the needle hub 210 can be aligned with the laser 206 (see FIG. 8B). Once the needle hub 210 is aligned with the laser 206, such that the needle hub 210, needle tip 212, and ureteroscope tip (not shown) within the kidney 200 form a single point trajectory on the C-arm 202 (see FIG. 8C), the surgeon can insert the needle 208 without any fluoroscopy activation or with greatly minimized fluoroscopy exposure used only to adjust for slight variations in respiratory excursion (see FIG. 8D). As shown in FIG. 8C, the laser 206 can be centered on the hub 210 of the needle, such that the hub 210 is illuminated, ensuring that the needle 208 is inserted at the appropriate trajectory. The depth of insertion can be determined based on a pre-operative CT scan or ultrasound measurements where the depth from the skin to the desired calix was measured. Alternatively, the desired depth of insertion can be marked on the needle 208 based on the initial images of the target using a mark or removable clip, tape or bracket. This bracket could be attached to the needle reversibly so that the needle would be inserted the desired depth, on the desired trajectory as directed by the laser beam. Once at the desired depth the bracket could be removed.

Once the needle 208 has been inserted, the C-arm 202 can be rotated and activated with a single pulse to confirm the depth of the needle. The C-arm 202 can be rotated to an angle relative to the vertical axis L-L that is on the opposite side of the vertical axis L-L from the needle insertion angle. The angle can be equal to the needle insertion angle. For example, if the desired insertion angle is about 30 degrees, the C-arm 202 can be rotated 60 degrees, such that the C-arm 202 is positioned 30 degrees relative to the vertical axis L-L opposite the needle insertion angle. Usually if the C-arm image intensifier is rotated 30 degrees toward the surgeon, the depth is checked by rotating the image intensifier to 30 degrees away from the surgeon. Additionally or alternatively, the surgeon can judge the depth by watching the ureteroscope image to determine under direct vision when the needle enters the collecting system.

With the needle in place, a wire can be passed from the insertion needle into the collecting system. The direct endoscopic vision of the internal tip of the needle can facilitate placement of the guide wire.

In certain aspects, an end of the guide wire can be grasped with a basket passed in a retrograde fashion through the ureteroscope and used to grasp the guide wire as described above. This basket can be used to pull the wire down the ureter to establish through and through access out the urethra, or alternatively to establish access only into the proximal ureter beyond the level of any stone or obstruction. The basket can include features similar to the basket catheter shown in FIG. 2.

In certain aspects, a ureteral access sheath can be placed in a retrograde fashion using a completely fluoro-less or minimal fluoroscopy technique. This ureteral access sheath allows the ureteroscope to be re-inserted into the kidney multiple times.

After positioning the guide wire, the guide wire can be converted to a conventional or stiff wire for subsequent dilation of the tract from the skin into the collecting system. The skin can be incised with a scalpel to the desired size depending on the size of the sheath employed for dilation. Next, the dilating balloon or serial dilation device can be placed at the correct depth using the ureteroscope under direct vision to avoid the use of fluoroscopy.

The ureteroscope would be used to watch the tip of the balloon catheter enter the collecting system of the kidney and then to position the dilating balloon or serial dilator so that the maximal dilation occurs just inside the edge of the caliceal collecting system. The correct depth could be determined on the first dilator if serial dilation was going to be performed and this depth used to insert the subsequent dilators using a bracket, using preplaced markings placed upon the dilators or a mark placed upon the dilators during surgery. If a balloon is used for dilation, the balloon can then be inflated to the appropriate pressure for full dilation, and the sheath can be placed into the kidney under direct ureteroscopic visualization. Alternatively, fluoroscopy could be used to position the sheath in a conventional manner or using a dramatically reduced fluoroscopic technique.

With the correct position of the sheath confirmed ureteroscopically, the procedure to remove the stone can commence in the standard fashion. Flexible and rigid nephroscopy accompanied by use of ultrasound, laser, and/or basketing can be used to remove the stone fragments. At the conclusion of the procedure, the kidney can be evaluated by flexible nephroscopy and ureteroscopy to confirm the absence of residual fragments. Intraoperative ultrasound can also be used to look for residual stones.

After the removal of all stones, a single pulse of conventional fluoroscopy can be used to ensure complete fragment removal. This step can be omitted if the surgeon is sure there are no residual fragments following endoscopic renal mapping. Alternatively, renal ultrasound could be used to look for residual fragments.

If a tubeless technique is desired, the surgeon can remove all the tubes at the conclusion of the procedure. Alternatively, the surgeon can place an 8 or 10 French nephrostomy, or a 16, 18, or 22 F council-tipped catheter with a 5 French re-entry catheter inside the renal tract to allow for renal drainage and reentry at a later time if desired. These tubes can be placed entirely without image guidance using direct vision by the ureteroscope or with minimal use of single pulse fluoroscopy. In another option, the ureteral catheter could be placed into the kidney from above while monitoring the position of the proximal end of the catheter using a flexible nephroscope placed through the percutaneous access site.

In some methods, a ureteral stent (e.g., a multi-length stent between about 22 and about 32 cm long and/or about 6 FR) could be passed over a guide wire that was placed into the bladder using an angle tipped guide wire and a 4 FR glide catheter. In another configuration, the 0.038 guide wire can be used to insert the stent. The length of the stent can be calculated using a novel technique determining the ureteral length using the Pythagorean Theorem where ureter length is calculated by measuring the known coronal ureter length, left to right length, and anterior/posterior length. Alternatively, the length can be estimated by counting the number of axial slices on the CT scan and multiplying by the slice reconstruction and adding 20%. In this technique, the fixed length stent would be placed into the ureter from above and the stent would be advanced until the markings showing the location for the UPJ was identified. The distal stent coil in the bladder could be confirmed when the ureteroscope was pulled down into the bladder.

In certain aspects, an end-hole catheter can be placed cystoscopically into the ureter and used to inject diluted contrast into the collecting system of the kidney ranging from 1-99% dilution depending upon the desired density of the contrast. The desired calix can be selected using fluoroscopy and any of the previously described techniques mentioned in the preceding description could be used for establishing access into the kidney. For example, the C-arm can be rotated laterally between about 20 and about 30 degrees. The C-arm, clamp tip, and desired calix can be aligned, and the laser guide can be placed in the center of the needle hub and used to insert the needle in a steady controlled fashion. Using this technique, the surgeon can use his hands with no concern of radiation exposure since the laser guide is used to direct the needle. Aspiration of fluid or air can be used to confirm appropriate positioning in the calix. Thereafter, a lubricious wire can be fed down the ureter using minimal use of low-dose pulsed or conventional fluoroscopy.

In certain aspects, an ultrasound machine can be used to select percutaneously the appropriate desired posterior calix for access. The laser guide can be positioned in line with the access of the ultrasound guide. Alternatively, a separate laser guide can be lined up with the axis of the ultrasound guide for insertion of the probe.

In certain aspects, a laser guide can be placed on the CT scanner or CT fluoroscopy machine and the axis of the needle tract can be positioned in line with the laser as directed by the CT scanner.

In certain aspects, the laser guide can be placed on a CT scanner and a special non-ferromagnetic needle can be used for placement using CT fluoroscopy.

At various points of the procedure, fluoroscopy can be performed with a single pulse or a pulse rate of one pulse per second to visualize the tip of the ureteroscope, needle, and/or guide wire. This pulse rate is still significantly lower than the conventional pulse rate, which can be about 25-30 pulses per second. Using this technique, a surgeon can reduce the fluoroscopy time from an average of about 6 to about 7 minutes per procedure to less than about one minute. In certain aspects, the total fluoroscopy time can be between less than or equal to about ten seconds, less than or equal to about three seconds, or less than or equal to about 1 second, thus reducing the risk of cancer dramatically for the patient, surgeon and staff by dramatically reducing the radiation exposure.

Needle

FIG. 3-4 illustrates an exemplary embodiment of a needle assembly 30 configured for use with the methods described above. The needle 32 can define a lumen through which a stylet 38 can optionally extend. The stylet 38 can include a sharpened distal end to facilitate percutaneous access. The needle 32 can define a blunt distal tip 36 to avoid inadvertent injury after removal of the stylet. Although, in some embodiments, the distal tip of the needle 36 can be sharpened. Optionally, the tip 36 of the needle 32 and/or stylet 38 can be etched to create a prominent acoustic signal on ultrasound. In some embodiments, at least a portion of the needle 32 proximal to the tip 36 can have a square shape to increase the acoustic prominence of the needle (not shown).

A proximal portion of the stylet 38 can have a hub 34. The hub 34 can be disc-shaped (see FIG. 3) or have a greater depth (e.g., similar to main body 102 of FIG. 11). As shown in FIG. 4, an upper surface of the hub 34 can include a number of concentric rings 40 (e.g., two, three, or more) to help the surgeon accurately position the light source (e.g., laser). In some embodiments, at least a portion of the hub 34 (e.g., an outer portion of the hub 34 or the entire hub 34) can be formed from a non-opaque material (e.g., transparent or translucent material). For example, an outer portion of the hub 34 can be formed from a transparent material and a central portion of the hub 34 can be formed from an opaque material to help center the laser. In some embodiments, the hub 34 can include a diameter between about 1 cm and about 5 cm, e.g., about 2 cm.

The distance between each ring 40 placed on the surface of the needle stylet hub 34 can be at least about 1 mm and/or less than or equal to about 10 mm, e.g., about 5 mm. The distance between each ring can be substantially the same or vary.

As shown in FIG. 4, the hub 34 can include a crosshatch 42 to help the user identify the central axis of the needle assembly 30. In certain aspects, the distance between the central axis C and an end of the crosshatch 42 can be between about 0.5 mm and 5.0 mm, or between about 1.0 mm and about 2.0 mm. In certain aspects, the distance between the central axis C and an end of the crosshatch 42 can be about 2 mm, or about 1.5 mm.

Depending on the requirements of the procedure, the needle 32 can include a length of at least about 5 cm, at least or about 10 cm or less than or equal to about 20 cm. In certain aspects, the needle 32 can include a length between about 5 cm and about 20 cm, e.g., about 10 cm, about 15 cm, or about 20 cm. In certain aspects, the needle 32 can be as large as 12 gauge and/or less than or equal to about 25 gauge, e.g., about 18 gauge. The needle 32 can define a lumen configured to allow the passage of a wire between about 0.18 gauge and about 0.38 gauge, e.g., about 0.25 gauge.

In certain embodiments, the hub 34 can be transparent or translucent and include an opaque channel (not shown). For example, the opaque channel can be centrally disposed in the hub 34. An upper surface of the hub 34 can include an opening that would allow the passage of the light source through the opaque channel when the opaque channel is aligned with the light source. In some embodiments, the opaque channel can be between about 0.1 mm wide and about 2 mm wide. In some embodiments, the opaque channel can have a length between about 1 mm and 5 cm. The length to width ratio would be such that the angle that the needle 32 could deviate from the axis of the light source and still produce the illumination of the glowing hub portion 34 of the needle 32 would be a very small angle, e.g., between about 0.1 and 10 degrees, such as about 2 degrees, and preferably less than 1 degree. In some embodiments, the opaque channel can be lined with one or more reflectors. These reflectors can be constructed from metal, glass, mirrors or any reflective material that can reflect light toward the light source when the light source is not aligned with the opaque channel so that no light enters the transparent or translucent portion of the hub 34. If the surgeon visualizes the feedback of the light reflected back out of the opaque channel, the surgeon would recognize that the orientation of the needle 32 is not correct. In some embodiments, the core of the channel could be lined with a wound metal spring that could reflect the light back out when not correctly aligned as described above.

In certain variants, the needle assembly 30 can include no stylet 38. The distal end 36 of the needle 32 can include a sharpened end, and the hub 34 described above can connected to a proximal end of the needle 32.

Figure 9:
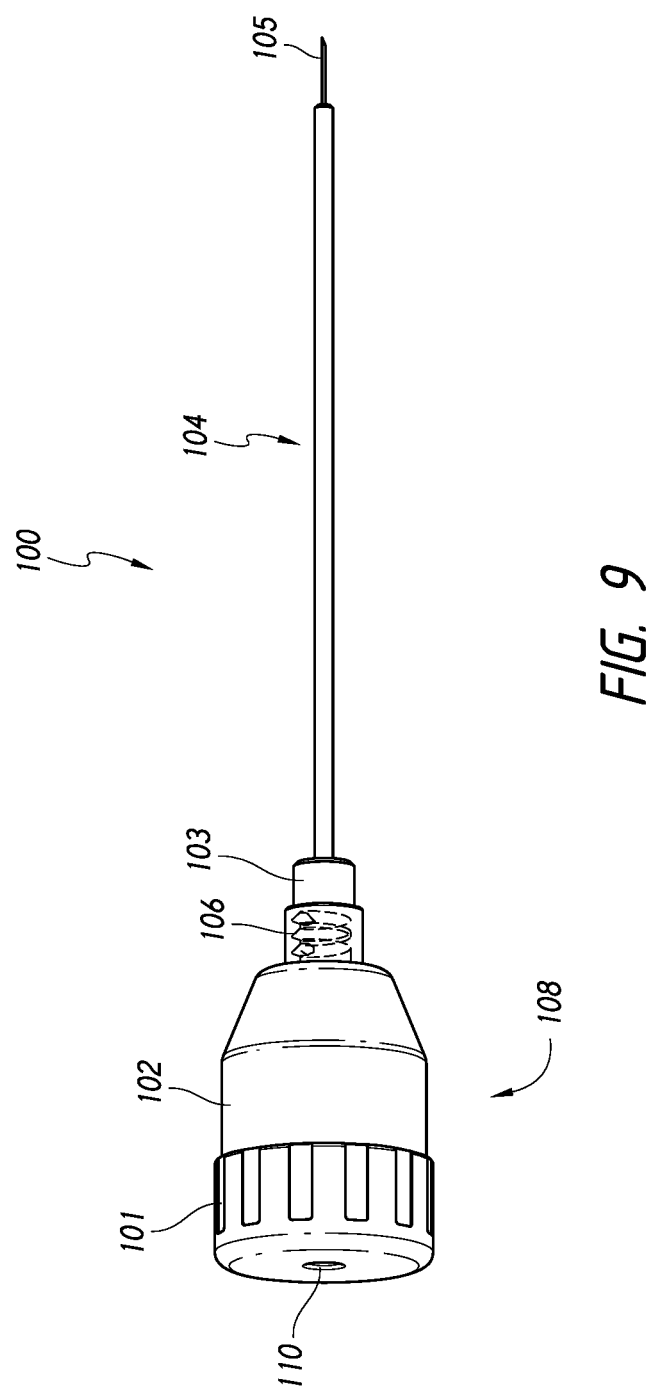
FIG. 9 illustrates a profile view of exemplary embodiment of a needle assembly that can be used with the methods described herein.
Figure 9A:
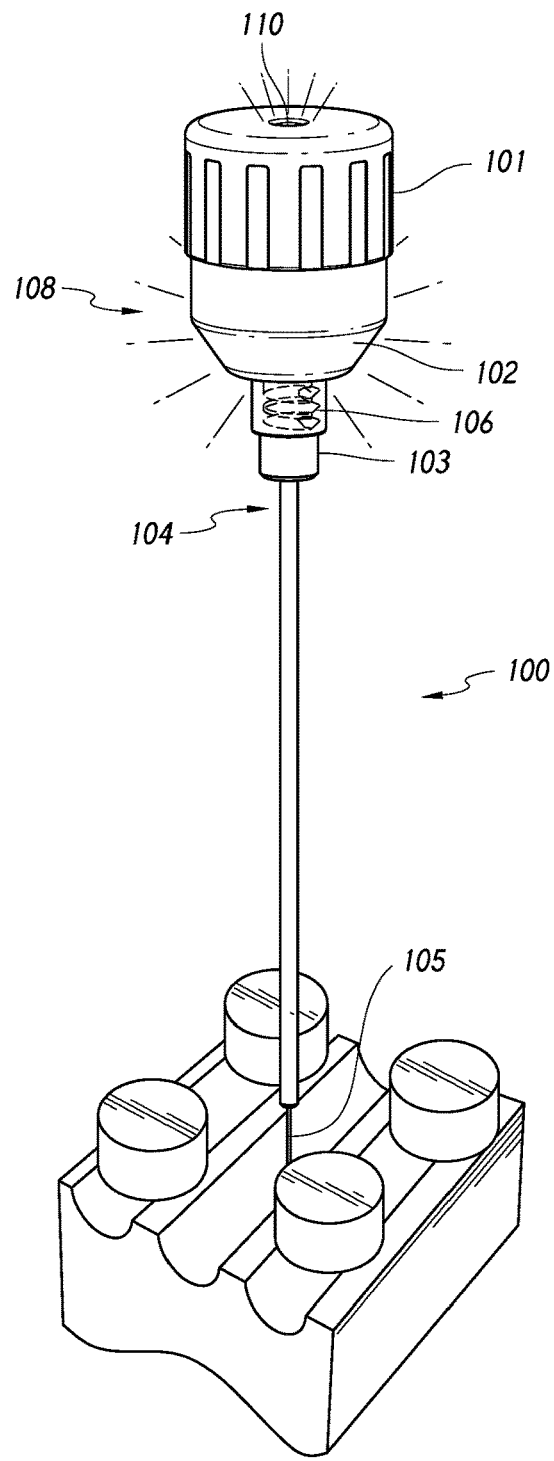
FIG. 9A illustrates the needle assembly shown in FIG. 9 in an illuminated configuration.

FIGS. 9 and 9A illustrate an exemplary embodiment of a percutaneous access needle assembly 100 that can be used with the methods described above. As described above, a laser can facilitate insertion and removal of the needle assembly 100 at the correct position and correct angle. When the needle assembly 100 is positioned correctly, the main housing 102 of the needle assembly 100 can light up up to indicate proper alignment with a light source (see FIG. 9). Use of the light source and needle assembly 100 to position the needle can reduce the total amount of fluoroscopy time by at least 50%.

Figure 10:
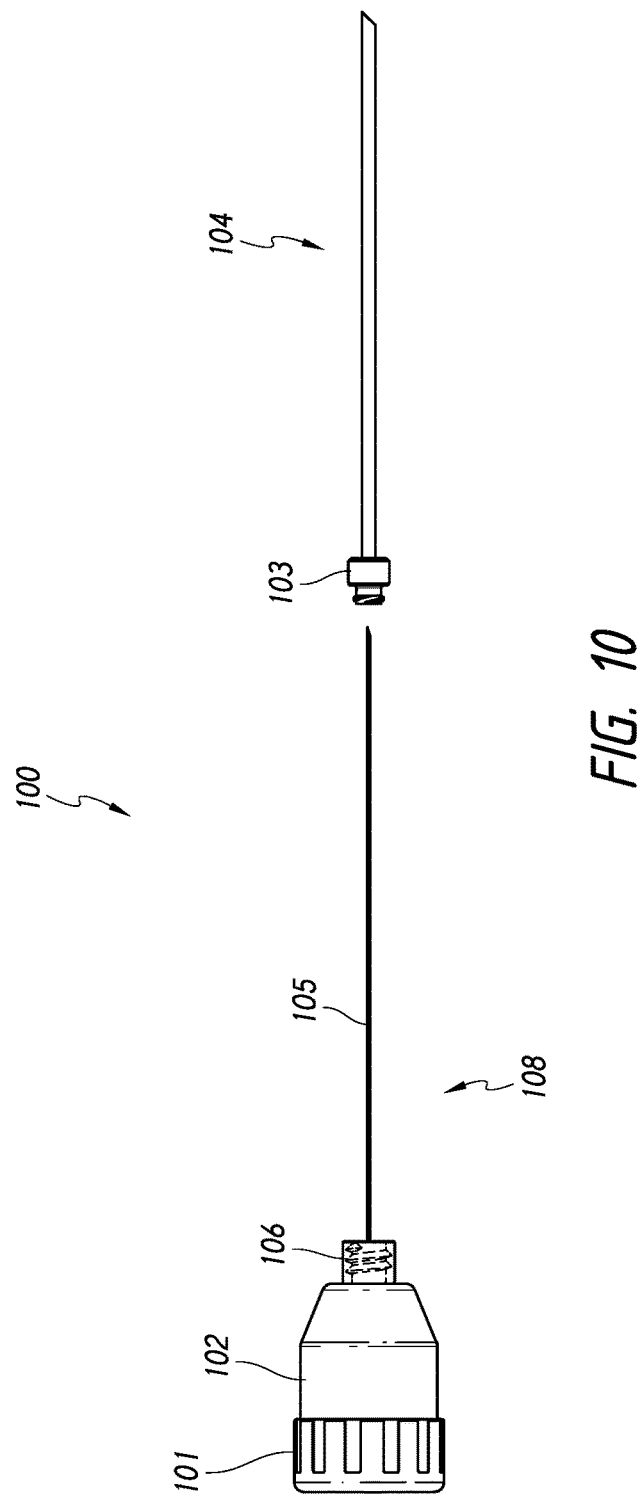
FIG. 10 illustrates a side view of the trocar needle and a cannula of the needle assembly shown in FIG. 9.
Figure 11:
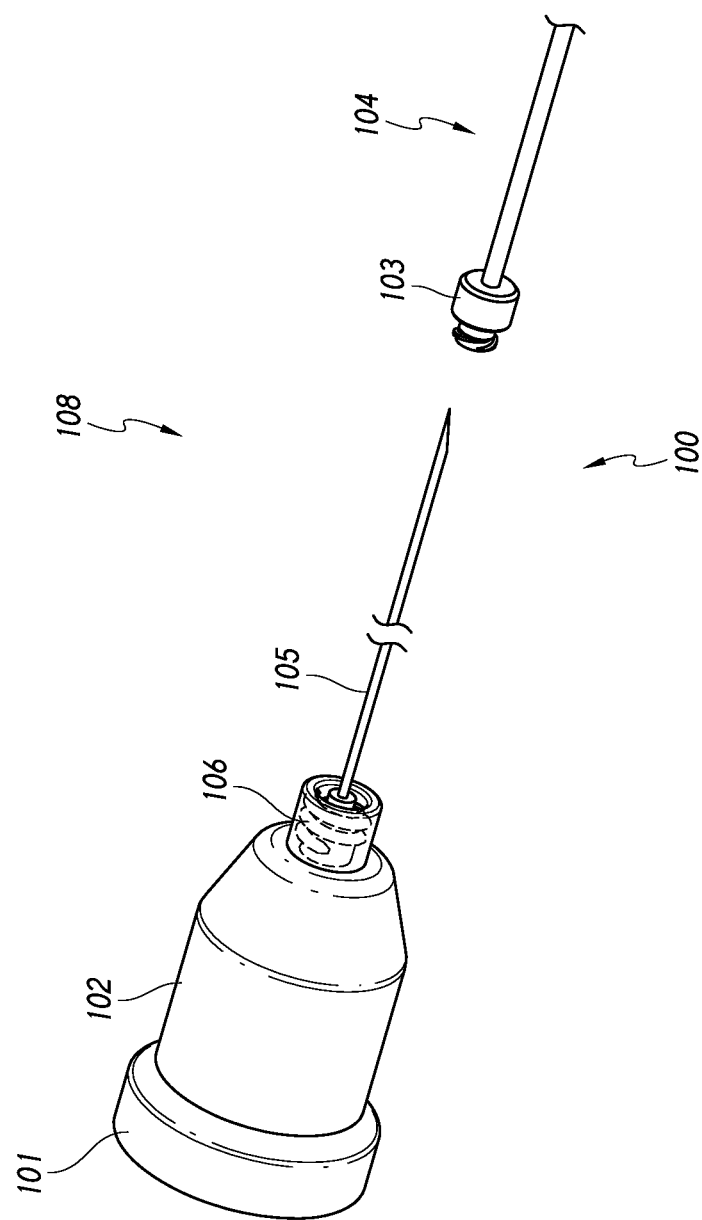
FIG. 11 illustrates a perspective view of the trocar needle and the cannula shown in FIG. 10.

As shown in FIGS. 10 and 11, the needle access assembly 100 can include a trocar needle 108 axially movable through a cannula 104 (see FIGS. 18A-18C). The trocar needle 108 can include a main housing 102 and a needle 105 extending from the main housing 102. In some embodiments, the needle 105, which is sharpened to allow for easy insertion, can optionally be detached from the trocar needle 108. For example, the needle 105 can connect directly or indirectly to the main housing 102 using a snap fit, friction fit, screw fit, adhesive, or other suitable connection. Further, the trocar 108 can optionally include an engagement feature 106 (see FIGS. 10 and 11) that can removably engage a corresponding engagement feature 103 of the blunt hollow needle cannula 104. For example, the needle assembly 100 can include a luer connector at a distal end of the main body 102. The luer connector 106 of the needle assembly 100 can engage a corresponding luer connector positioned at a proximal end of the cannula 104. Other connections are also imaginable, such as screw fit, a friction fit, a snap fit, or otherwise.

Figure 12:
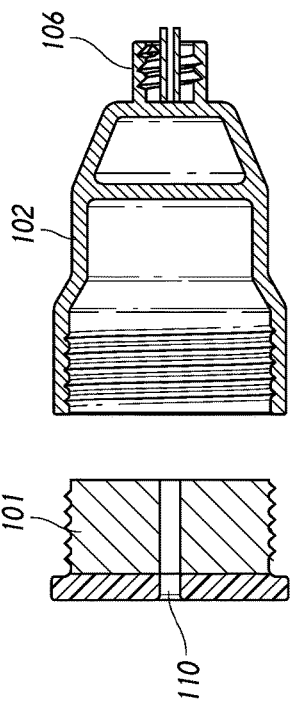
FIG. 12 illustrates a cross-sectional view of a cap and a proximal portion of an embodiment of a trocar needle.

As shown in FIG. 12, the trocar 108 can include a cap 101 through which a laser or other light source can be shined through an opening 110 to provide guidance for percutaneous access. The cap 101 can be opaque and can have the narrow, centrally disposed opening 110 extending through the cap 101. The opening 110 can have a diameter that is less than a diameter of the main body 102 (e.g., less than about 50%, less than about 40%, less than about 30%, less than about 20%, less than about 10%, or values in between). In some embodiments, the opening 110 can be optionally filled with a transparent material. In some embodiments, the cap 101 can optionally include a concentric circle pattern similar to the pattern described in connection with FIG. 4 to facilitate the positioning of the laser.

To facilitate visualization of the illuminated main body 102, the main body 102 can include a diameter of at least about 1 inch, at least about 2 inches, or preferably at least about 3 inches. In some embodiments, the main body 102 can be constructed from an opaque material, and the user can rely on alignment between the light source and opening 110 for visual indication of proper alignment. In some embodiments, the main body 102 can be constructed from a transparent or translucent material so that users can visualize the light source shining through the main body 102. Since the cap 101 is opaque, the main body 102 will only illuminate if the laser is aligned with the opening 110. This ensures that that the main body 102 is not illuminated when the laser enters the main body 102 but at an incorrect angle.

Figure 14A:
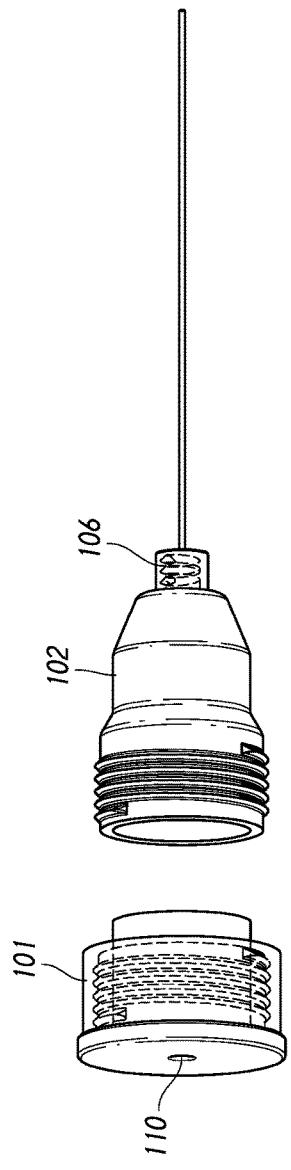
FIG. 14A illustrates another embodiment of a cap and a trocar needle.
Figure 14B:
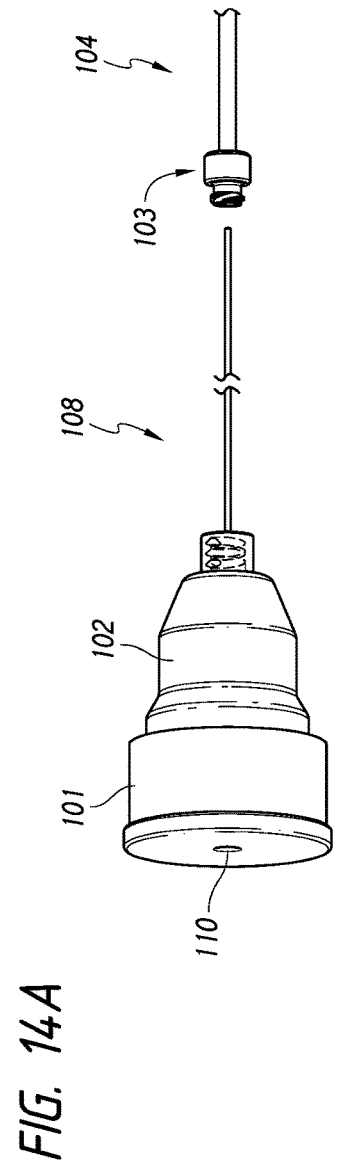
FIG. 14B illustrates a perspective view of a needle access assembly having the trocar needle shown in FIG. 14A and a cannula.
Figure 14C:
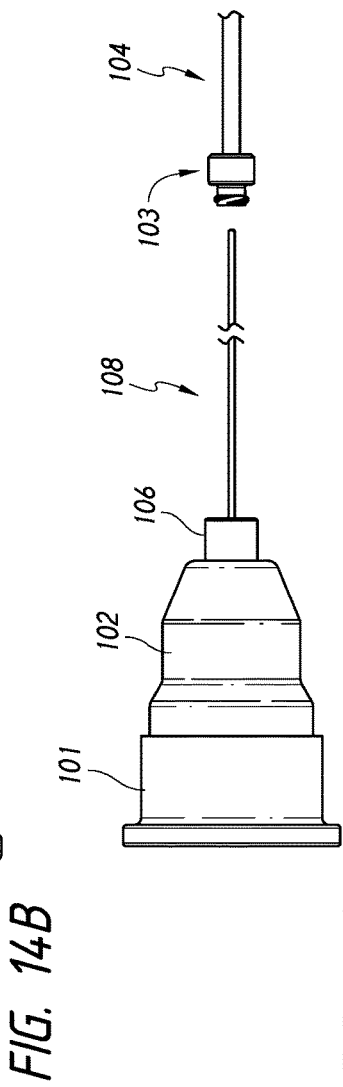
FIG. 14C illustrates a side view of the needle access assembly shown in FIG. 14B.

In some embodiments, the cap 101 can removably engage the main body 102. For example, the cap 101 can threadably engage the main body 102, such that the cap 101 fits into (see FIG. 12) and/or surrounds (see FIGS. 14A-14C) the main body 102. As another example, the cap 101 can engage the main body 102 using a snap fit (not shown) such that the cap 101 fits into and/or surrounds the main body 102. Alternatively, as shown in FIGS. 15A-15D, the cap 101 and main body 102 can be integrally formed.

Figure 13A:
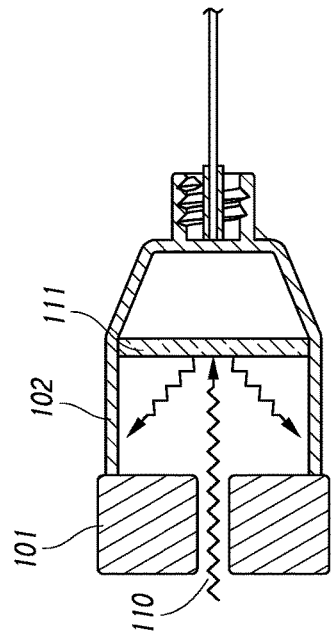
FIG. 13A illustrates a cross-sectional view of an embodiment of a trocar needle having a reflective coating plate.
Figure 13B:
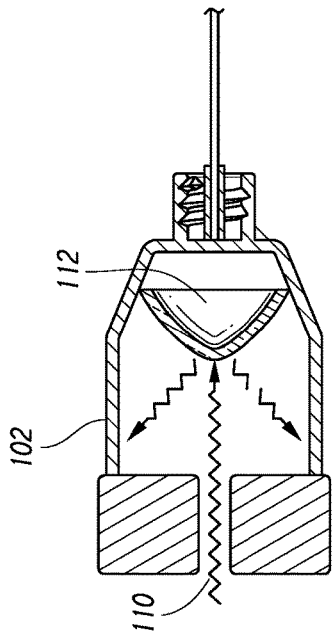
FIG. 13B illustrates a cross-sectional view of an embodiment of a trocar needle having a dome reflector.
Figure 16:
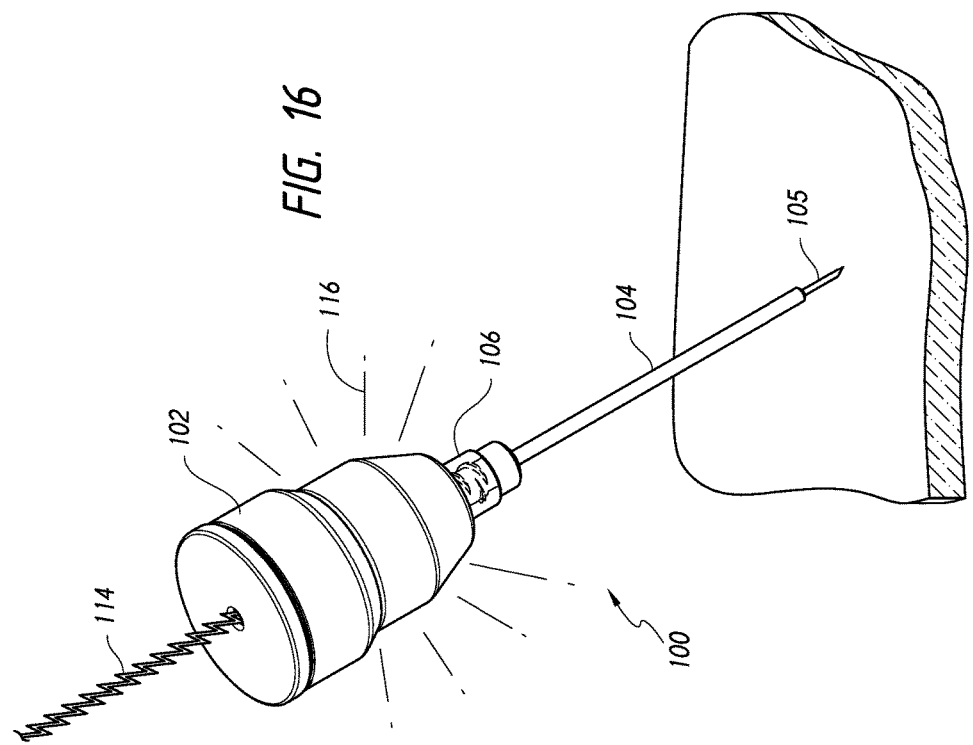
FIG. 16 illustrates a perspective view of an exemplary embodiment of the assembly indicating that the assembly is properly aligned.
Figure 15D:
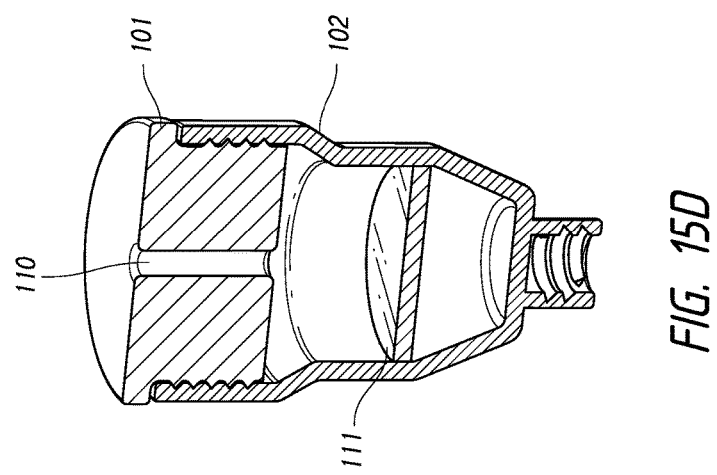
FIG. 15D illustrates a partial cross-section of a proximal portion of the trocar needle shown in FIG. 15A.

As shown in FIGS. 13A and 13B, the main body 102 of the trocar 108 can optionally include a light enhancement feature for propagating light. In some embodiments, as shown in FIG. 13A, a reflective plate, reflecting coating, otherwise reflective surface 111 can be provided within an interior space of the main body 102. In some embodiments, as shown in FIG. 13B, a dome reflector 112 can be positioned within the main housing 102. As shown in FIG. 16, when the needle access assembly 100 is aligned with the light source 114, the light enhancement feature can propagate light 116 such that there is clear visual indication of proper alignment. In contrast, as shown in FIG. 17, when the needle access assembly 100 is not properly aligned with the light source 114, little or no light can be seen from the main housing 102.

Although not shown, in some embodiments, the needle access assembly 100 can include a camera to provide direct visualization during insertion. In some embodiments, the needle access assembly 100 can include sensors in a 3D array to provide real time data on 3D movement of the needle access assembly 100.

Training Model

Figure 5:
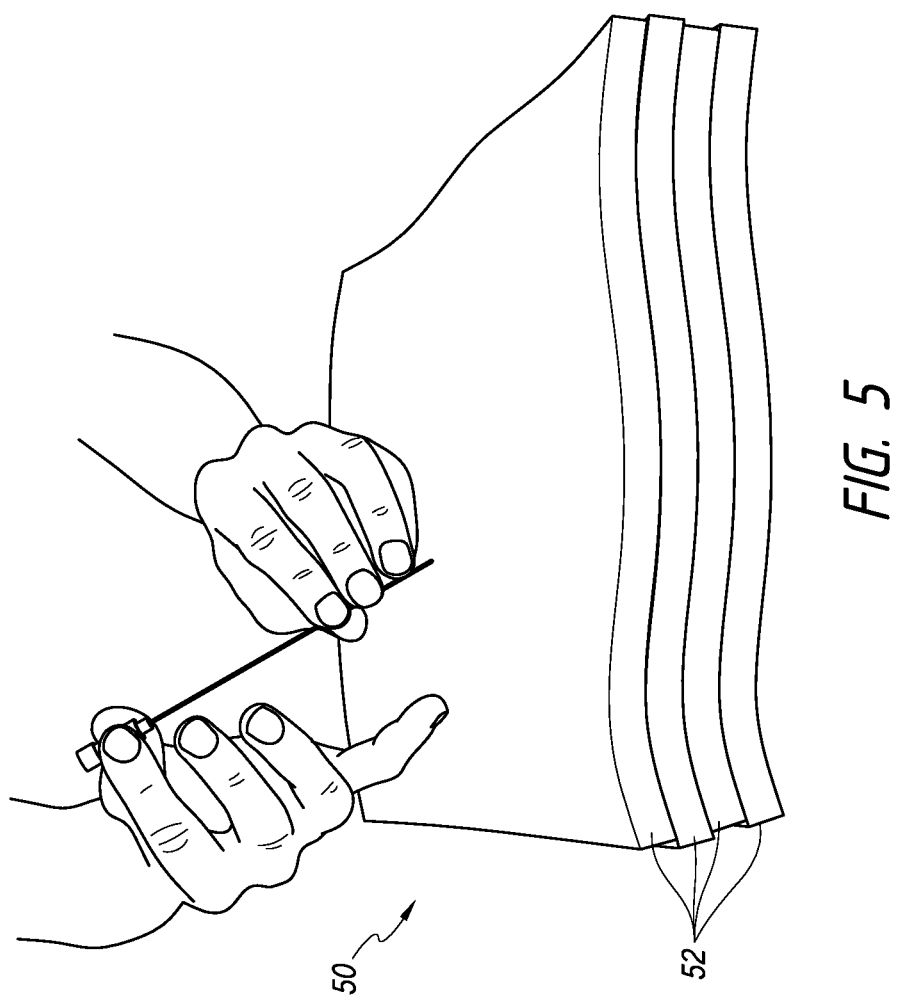
FIGS. 5-7 illustrate a training model for percutaneous surgical access training.
Figure 6:
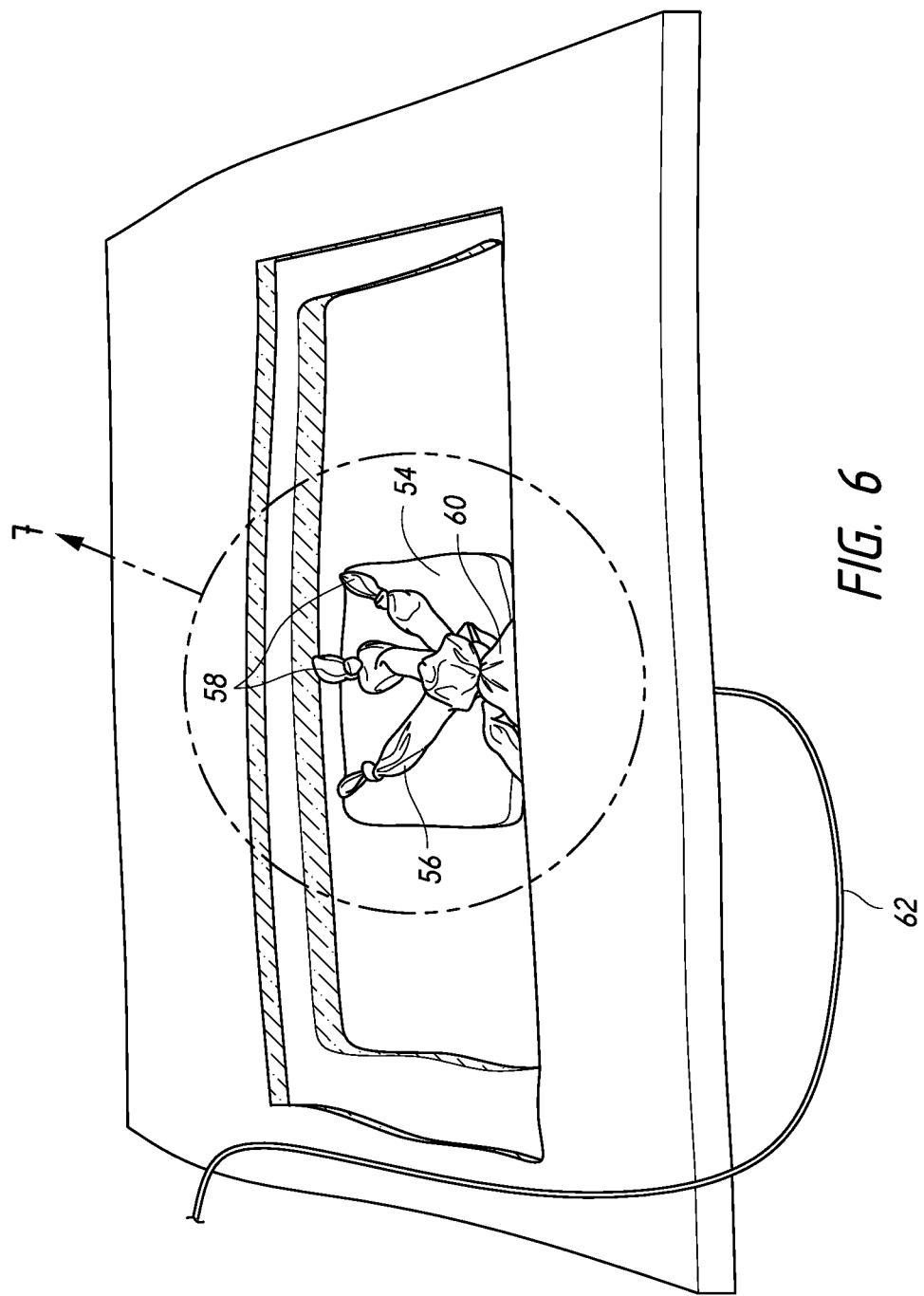
Figure 7:
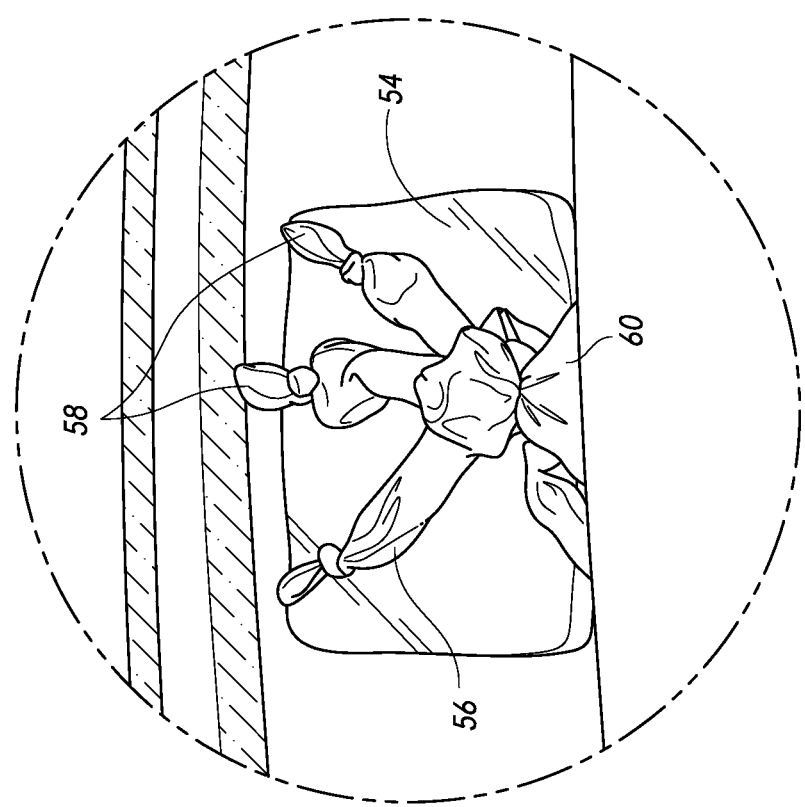

FIGS. 5-7 illustrate a training model 50 for training users how to obtain percutaneous access using the above-described technique. The model 50 can include one or more layers 52 designed to replicate the organs, muscle, fat, and skin. FIGS. 5-7 specifically illustrate a model 50 for the kidney collecting system, but similar materials can be used to construct a model for other areas of the body.

The model 50 can include one or more layers designed to replicate the skin. The skin layers can include, but are not limited to, carpet padding, plastic, or silicone. The deep muscles and perinephric fat can be replicated using gelatin, silicone, or any polymer or substance that will permit shaping into the desired shape. The model collecting system 56 can be replicated using a latex or any type of glove. The fingers 58 can be tied off to create the calices, and tape can be applied to the innermost portions of the fingers to create the narrowing of the infundibula. The palm of the glove 60 can be narrowed by tying or using tape to create a renal pelvis. The palm of the glove 60 can be connected to a penrose drain 62 to establish the ureter. The model kidney 54 can be replicated by forming reniform shape from a gelatin, soft plastic, silicone, or other soft material. The kidney material can be made of clear material to allow an observer to determine if the trainee had placed the needle into the appropriate calix by visual inspection from underneath a glass surface. In some embodiments, the model 50 could include a small camera on the inside to simulate the image provided by the ureteroscope and to allow the trainee to learn how the internal image may assist in correct placement of the needle.

The layers 52 can be mounted on a surface constructed from a clear material, for example, plexiglass. One or more holes can be formed in the clear surface. Each of the holes can receive a bolt or other structure to secure and align each of the layers to the clear surface.

The model can be positioned on the cut out portion of the fluoroscopy table, so the observer can easily see if the needle had been placed into the appropriate calix by direct observation. An open-ended catheter can be used to create the contrast used for injection if the training would like to focus on learning the fluoroscopy guided laser DARRT technique.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments, whether these features, elements, and/or steps are included or are to be performed in any particular embodiment.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

Although certain embodiments and examples have been described herein, it will be understood by those skilled in the art that many aspects of the methods and devices shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "aligning a needle with a light source" include "instructing alignment of a needle and a light source."

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "about 3 mm" includes "3 mm."

Example Embodiments

The following example embodiments identify some possible permutations of combinations of features disclosed herein, although other permutations of combinations of features are also possible.

1. A needle access device configured for insertion into a patient with reduced fluoroscopy, the device comprising:
  a needle connected to a hub portion, the hub portion comprising:

an opaque cap portion;
a non-opaque body portion positioned between the opaque cap portion and the needle; and
a channel extending through the opaque cap portion, the channel positioned such that the non-opaque body portion only illuminates when a light source is aligned with the channel.

2. The needle access device of Embodiment 1, wherein the channel has a diameter that is less than or equal to an outer diameter of the needle.

3. The needle access device of Embodiment 1 or 2, wherein the hub portion comprises a reflective surface positioned in the non-opaque body portion.

4. The needle access device of Embodiment 3, wherein the reflective surface comprises a reflective material.

5. The needle access device of Embodiment 3, wherein the reflective surface comprises a dome reflector.

6. The needle access device of any one of Embodiments 3 to 5, wherein the reflective surface is positioned across a transverse plane of the hub portion.

7. The needle access device of any one of the preceding Embodiments, further comprising at least two concentric circles disposed on a proximal end of the hub portion.

8. The needle access device of any one of the preceding Embodiments, further comprising a crosshatch disposed on a proximal end of the hub portion.

9. The needle access device of any one of the preceding Embodiments, wherein the hub portion further comprises a luer connector configured to connect to a cannula.

10. The needle access device of any one of the preceding Embodiments, wherein the opaque cap portion is removably secured to the non-opaque body portion.

11. The needle access device of Embodiment 10, wherein the opaque cap portion is threadably secured to the non-opaque body portion.

12. The needle access device of any one of the preceding Embodiments, wherein an inner diameter of the non-opaque body portion is larger than a diameter of the channel.

13. The needle access device of any one of the preceding Embodiments, wherein an outer diameter of the non-opaque body portion is at least two times larger than an outer diameter of the needle.

14. The needle access device of any one of the preceding Embodiments, wherein an outer diameter of the non-opaque body portion is at least five times larger than an outer diameter of the needle.

15. The needle access device of any one of the preceding Embodiments, wherein the non-opaque body portion is transparent.

16. The needle access device of any one of Embodiments 1 to 15, wherein the non-opaque body portion is translucent.

17. A method of obtaining percutaneous needle access:
selecting a calix for percutaneous access;
positioning a flexible ureteroscope in the selected calix;
directing a light source at a desired needle-insertion angle and in line with a tip of the ureteroscope;
aligning the needle access device of any one of Embodiments 1 to 16 with the light source and the ureteroscope tip; and
inserting the needle access device into the selected calix.

18. The method of Embodiment 17, further comprising delivering an instrument through the ureteroscope, the instrument configured to facilitate the insertion of the needle through the selected calix.

19. The method of Embodiment 18, wherein the instrument is identifiable under ultrasound.

20. The method of Embodiment 18 or 19, wherein the instrument is a balloon catheter.

21. The method of Embodiment 18 or 19, wherein the instrument is a basket catheter.

22. The method of any one of Embodiments 17 to 21, further comprising applying fluoroscopy for less than ten seconds.

23. The method of any one of Embodiments 17 to 22, wherein aligning the needle access device with the light source comprises illuminating a hub portion of the needle access device.

24. The method of Embodiment 23, wherein illuminating the hub portion of the needle access device comprises reflecting the light source from a reflective surface within the hub portion.

25. The method of any one of Embodiments 17 to 24, wherein the light source is a laser beam.

26. The method of any one of Embodiments 17 to 25, wherein inserting the needle access device into the selected calix comprises advancing the needle through a cannula.

What is claimed is:

1. A needle access device configured for insertion into a patient with reduced fluoroscopy, the device comprising:
a needle connected to a hub portion, the hub portion comprising:
an opaque cap portion;
a non-opaque body portion positioned between the opaque cap portion and the needle;
a reflective surface positioned in the non-opaque body portion, wherein the reflective surface comprises a dome reflector; and
a channel extending through the opaque cap portion, the channel positioned such that the non-opaque body portion only illuminates when a light source is aligned with the channel.

2. The needle access device of claim 1, wherein the channel has a diameter that is less than or equal to an outer diameter of the needle.

3. The needle access device of claim 1, wherein the reflective surface is positioned across a transverse plane of the hub portion.

4. The needle access device of claim 1, further comprising at least two concentric circles disposed on a proximal end of the hub portion.

5. The needle access device of claim 1, further comprising a crosshatch disposed on a proximal end of the hub portion.

6. The needle access device of claim 1, wherein the hub portion further comprises a luer connector configured to connect to a cannula.

7. The needle access device of claim 1, wherein the opaque cap portion is removably secured to the non-opaque body portion.

8. The needle access device of claim 7, wherein the opaque cap portion is threadably secured to the non-opaque body portion.

9. The needle access device of claim 1, wherein an inner diameter of the non-opaque body portion is larger than a diameter of the channel.

10. The needle access device of claim 1, wherein an outer diameter of the non-opaque body portion is at least two times larger than an outer diameter of the needle.

11. The needle access device of claim 1, wherein an outer diameter of the non-opaque body portion is at least five times larger than an outer diameter of the needle.

12. The needle access device of claim 1, wherein the non-opaque body portion is translucent.

13. The needle access device of claim 1, wherein the non-opaque body portion is transparent.

\* \* \* \* \*